United States Patent
Bernal et al.

(10) Patent No.: US 12,279,757 B2
(45) Date of Patent: Apr. 22, 2025

(54) CARPAL TUNNEL RELEASE SURGICAL TOOL WITH WIRELESS VIDEO CAPABILITY

(71) Applicant: Blue Ocean BBB, LLC, Houston, TX (US)

(72) Inventors: Rafael R. Bernal, Houston, TX (US); Marcos V. Masson, Houston, TX (US); Yevgeny Shuhatovich, Houston, TX (US)

(73) Assignee: Blue Ocean BBB, LLC, Houston, TX (US)

( * ) Notice: Subject to any disclaimer, the term of this patent is extended or adjusted under 35 U.S.C. 154(b) by 873 days.

(21) Appl. No.: 17/414,865

(22) PCT Filed: Mar. 26, 2020

(86) PCT No.: PCT/US2020/024944
§ 371 (c)(1),
(2) Date: Jun. 16, 2021

(87) PCT Pub. No.: WO2020/198465
PCT Pub. Date: Oct. 1, 2020

(65) Prior Publication Data
US 2022/0054160 A1 Feb. 24, 2022

Related U.S. Application Data

(60) Provisional application No. 62/824,816, filed on Mar. 27, 2019.

(51) Int. Cl.
*A61B 1/04* (2006.01)
*A61B 1/00* (2006.01)
(Continued)

(52) U.S. Cl.
CPC .......... *A61B 1/07* (2013.01); *A61B 1/00016* (2013.01); *A61B 1/00032* (2013.01);
(Continued)

(58) Field of Classification Search
USPC .................................................. 600/183, 133
See application file for complete search history.

(56) References Cited

U.S. PATENT DOCUMENTS 4,962,770 A  10/1990  Agee et al.
4,963,147 A  10/1990  Agee et al.
(Continued)

FOREIGN PATENT DOCUMENTS

CN    203436371 U    2/2014
CN    207400799 U    5/2018
(Continued)

OTHER PUBLICATIONS

MicroAire Surgical Instruments, LLC, SmartRelease® Endoscopic Carpal Tunnel Release (ECTR), https://www.microaire.com/wp-content/uploads/2017/03/LIT-ECTR-SALES-REV-D.pdf (2017).
(Continued)

*Primary Examiner* — John P Leubecker
(74) *Attorney, Agent, or Firm* — Lewis & Reese, PLLC

(57) ABSTRACT

A Carpal Tunnel Release (CTR) surgical tool is disclosed. The CRT tool is useable to perform CTR surgically endoscopically through an incision in the patient, and includes dedicated optical components within the tool. The tool also includes wireless communication means to broadcast video images from the camera to an external display without the use of any cabling. The CTR tool is modular, thus allowing different portions of the tool to be replaced, including a blade tip assembly. The CTR tool is comprised of components manufactured of materials that can be cleaned and sterilized using an autoclave alone, which allows the tool to
(Continued)

be more easily and cheaply used in subsequent surgeries, and in contexts that may lack the resources and support traditionally necessary for surgery. The CTR system may simply comprise of the tool (and its cheaper replacement parts), a monitor having wireless capability, and a simple autoclave.

21 Claims, 20 Drawing Sheets

(51) Int. Cl.
| | |
|---|---|
| A61B 1/055 | (2006.01) |
| A61B 1/06 | (2006.01) |
| A61B 1/07 | (2006.01) |
| A61B 17/32 | (2006.01) |
| H04N 5/38 | (2006.01) |
| H04N 7/18 | (2006.01) |
| H04N 23/51 | (2023.01) |
| H04N 23/55 | (2023.01) |
| H04N 23/56 | (2023.01) |
| A61B 17/00 | (2006.01) |
| H04N 23/50 | (2023.01) |

(52) U.S. Cl.
CPC ...... *A61B 1/00066* (2013.01); *A61B 1/00096* (2013.01); *A61B 1/00105* (2013.01); *A61B 1/042* (2013.01); *A61B 1/055* (2013.01); *A61B 1/0669* (2013.01); *A61B 17/320016* (2013.01); *H04N 5/38* (2013.01); *H04N 7/183* (2013.01); *H04N 23/51* (2023.01); *H04N 23/55* (2023.01); *H04N 23/56* (2023.01); *A61B 1/00009* (2013.01); *A61B 2017/00296* (2013.01); *A61B 2017/00473* (2013.01); *H04N 23/555* (2023.01)

(56) References Cited

U.S. PATENT DOCUMENTS

| | | |
|---|---|---|
| 5,089,000 A | 2/1992 | Agee et al. |
| 5,269,796 A | 12/1993 | Miller et al. |
| 5,306,284 A | 4/1994 | Agee et al. |
| 5,366,465 A | 11/1994 | Mirza |
| 5,387,222 A | 2/1995 | Strickland |
| 5,425,355 A * | 6/1995 | Kulick ............... A61B 18/24 606/17 |
| 5,458,611 A | 10/1995 | Resnick et al. |
| 5,499,992 A | 3/1996 | Meade et al. |
| 5,549,623 A | 8/1996 | Sharpe et al. |
| 5,569,283 A | 10/1996 | Green et al. |
| 5,611,808 A | 3/1997 | Hossain et al. |
| 5,649,946 A | 7/1997 | Bramlet |
| 5,651,790 A | 7/1997 | Resnick et al. |
| 5,667,472 A | 9/1997 | Finn et al. |
| 5,667,473 A | 9/1997 | Finn et al. |
| 5,908,433 A | 6/1999 | Eager et al. |
| 5,968,061 A | 10/1999 | Mirza |
| 6,019,774 A | 2/2000 | Weiss et al. |
| 6,730,081 B1 | 5/2004 | Desai |
| 7,303,555 B2 | 12/2007 | Makin et al. |
| 7,628,798 B1 | 12/2009 | Welborn |
| 7,780,690 B2 | 8/2010 | Rehnke |
| 7,918,784 B2 | 4/2011 | Wellborn et al. |
| 8,273,098 B2 | 9/2012 | Strickland |
| 8,419,728 B2 | 4/2013 | Klotz et al. |
| 8,523,891 B2 | 9/2013 | Welborn |
| 8,523,892 B2 | 9/2013 | Rehnke et al. |
| 8,603,124 B1 | 12/2013 | Hatch |
| 8,672,960 B2 | 3/2014 | Briganti et al. |
| 8,951,273 B1 | 2/2015 | Fard |
| 8,992,424 B2 | 3/2015 | Orbay et al. |
| 9,066,746 B2 | 6/2015 | Mirza et al. |
| 9,108,005 B2 | 8/2015 | Agee et al. |
| 9,144,433 B2 | 9/2015 | Mirza et al. |
| 9,179,930 B2 | 11/2015 | Mirza et al. |
| 9,642,643 B1 | 5/2017 | Jurbala |
| 9,968,240 B2 | 5/2018 | Agee et al. |
| 10,874,287 B2 * | 12/2020 | Ouyang ............... A61B 1/0684 |
| 2003/0078476 A1 * | 4/2003 | Hill .................. A61B 1/267 600/109 |
| 2004/0111012 A1 * | 6/2004 | Whitman ............. A61B 1/0052 600/179 |
| 2004/0162572 A1 | 8/2004 | Sauer |
| 2005/0177024 A1 * | 8/2005 | Mackin ............. A61B 1/00016 600/109 |
| 2007/0167678 A1 * | 7/2007 | Moskowitz ........ A61B 1/00016 600/104 |
| 2008/0139881 A1 * | 6/2008 | Cover .................... H04N 7/185 600/103 |
| 2008/0195128 A1 * | 8/2008 | Orbay ................ A61B 1/00048 600/183 |
| 2008/0200758 A1 | 8/2008 | Orbay et al. |
| 2011/0009694 A1 | 1/2011 | Schultz et al. |
| 2011/0018988 A1 * | 1/2011 | Kazakevich ....... G02B 23/2484 348/E7.085 |
| 2011/0270034 A1 * | 11/2011 | Mackin ................. A61M 16/04 600/112 |
| 2014/0031621 A1 | 1/2014 | Liu |
| 2014/0121456 A1 | 5/2014 | McCormack et al. |
| 2014/0213848 A1 * | 7/2014 | Moskowitz ............. A61B 17/29 600/106 |
| 2014/0288371 A1 * | 9/2014 | Nakatate ................ A61B 1/015 600/156 |
| 2015/0060516 A1 | 3/2015 | Collings et al. |
| 2015/0320436 A1 * | 11/2015 | Agee .................. A61B 1/00087 600/104 |
| 2016/0278615 A1 | 9/2016 | Kawula et al. |
| 2017/0265879 A1 * | 9/2017 | Washburn, II ......... A61B 1/317 |
| 2017/0290500 A1 * | 10/2017 | Alexander ......... A61B 1/00009 |
| 2018/0317999 A1 | 11/2018 | Park et al. |

FOREIGN PATENT DOCUMENTS

| | | |
|---|---|---|
| CN | 108618830 A | 10/2018 |
| EP | 0308258 | 3/1989 |
| WO | 2016/137838 A1 | 9/2016 |
| WO | 2018/129167 | 7/2018 |

OTHER PUBLICATIONS

Endoscopic Carpal Tunnel Release, http://www.endodoctor.de/reparatur-endoskop/endoscopic-carpal-tunnel-release/?lang=en (Jan. 30, 2018).

SegWay Orthopaedics, Inc., Synchronized Endoscopic Guide System for Endoscopic Carpal Tunnel Release, Surgical Technique, http://segwayortho.com/segway1/Documents/SEG-WAY%20Surgical%20Technique%20MKT100-0131.pdf.

Smith & Nephew Ectra II Carpal Ligament System Brochure, http://www.smith-nephew.com/global/assets/pdf/products/surgical/ectraii_brochure.pdf (2004).

Stratos Endoscopic Release System, Endoscopic Carpal Tunnel Release, Surgical Technique, http://www.amsurgical.com/stratos/files/Stratos_ECTR_ProxTechniqueGuide_Digi.pdf (2014).

Arthrex, Inc., Centerline™ Endoscopic Carpal Tunnel Release, Surgical Technique (2014).

Sonex Health, LLC, Micro-invasive Carpal Tunnel Release with the SX-One MicroKnife, https://www.sonexhealth.com/the-sx-one-microknife (2017).

International Search Report and Written Opinion regarding corresponding PCT Application No. PCT/US2020/024944, mailed Jun. 22, 2020.

Extended European Search Report regarding corresponding European Patent Application No. 20779776.2, mailed Sep. 27, 2022.

(56) References Cited

OTHER PUBLICATIONS

First Notice of Examination Action regarding corresponding Chinese Patent Application No. 202080025361.5, mailed Mar. 27, 2024.

* cited by examiner

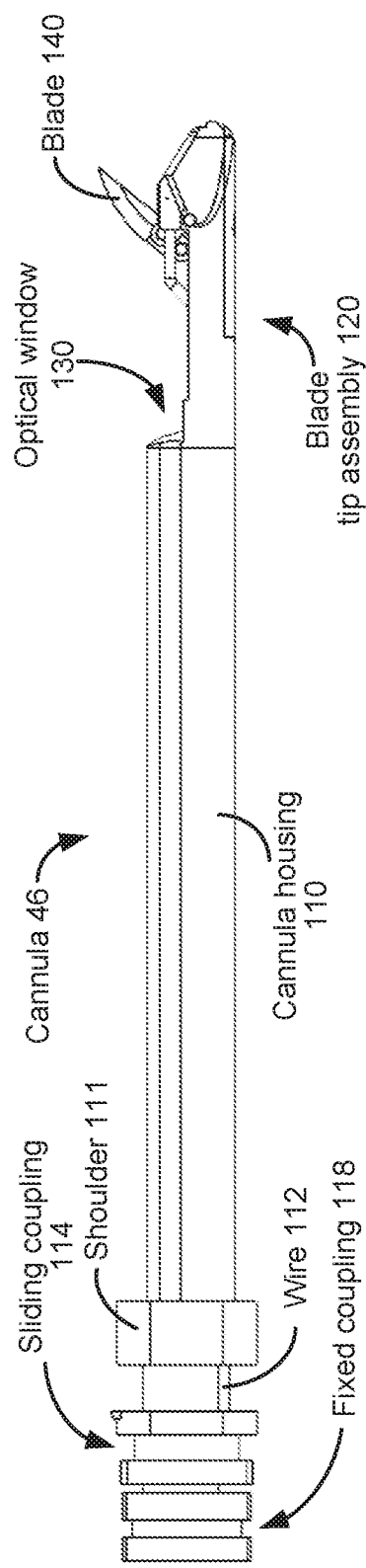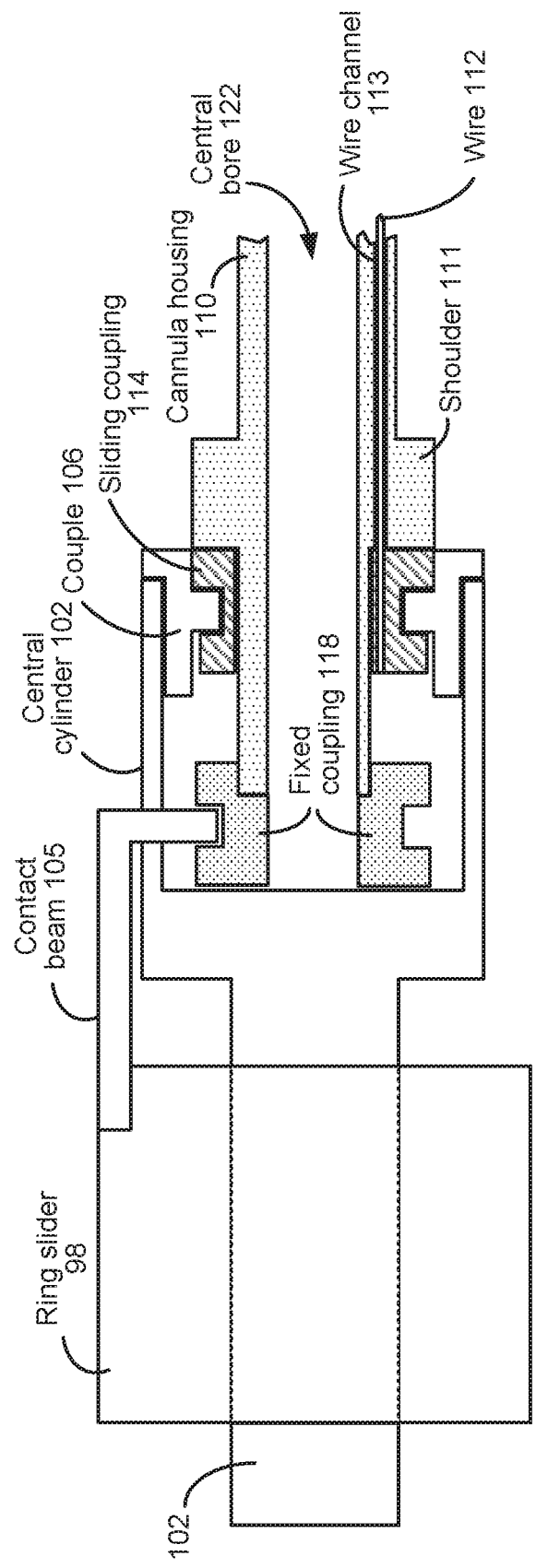
Figure 11

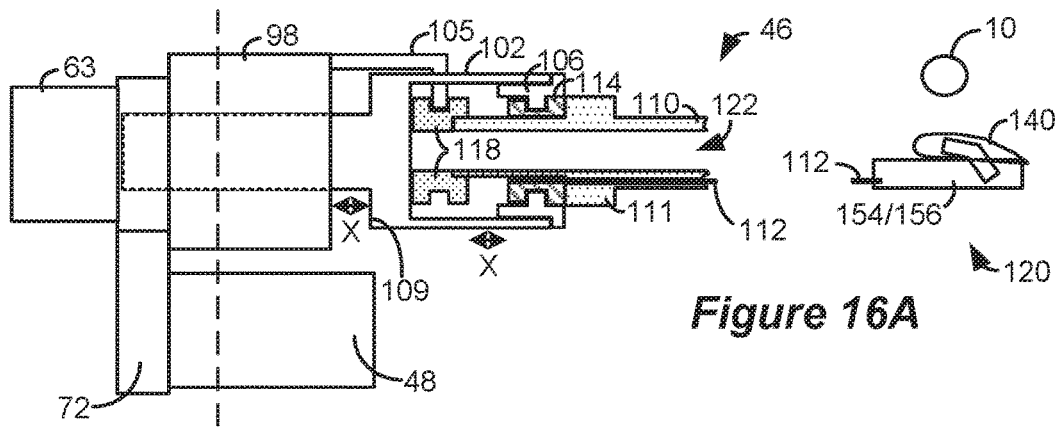
*Figure 16A*
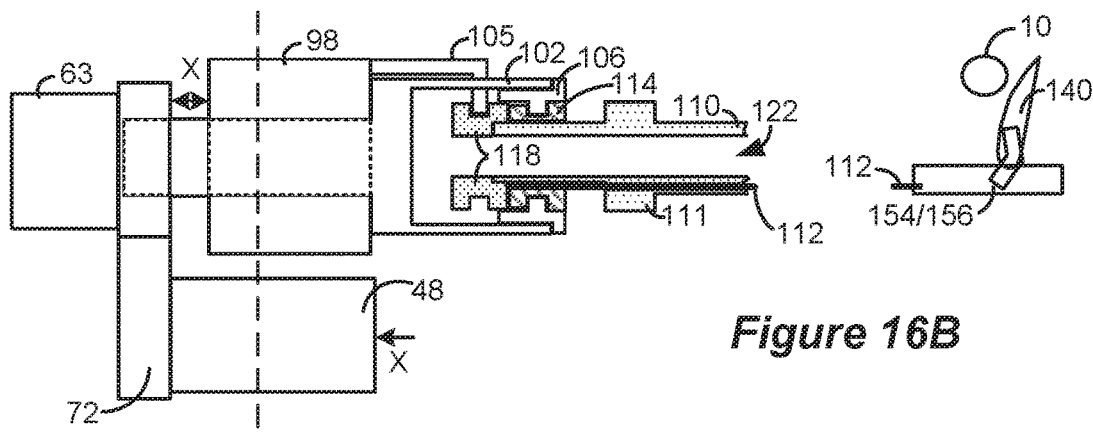
*Figure 16B*
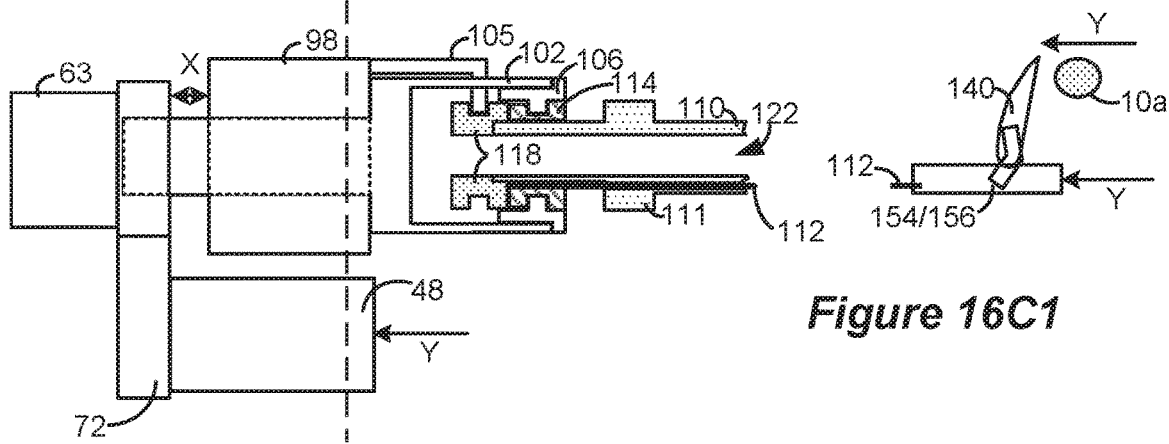
*Figure 16C1*

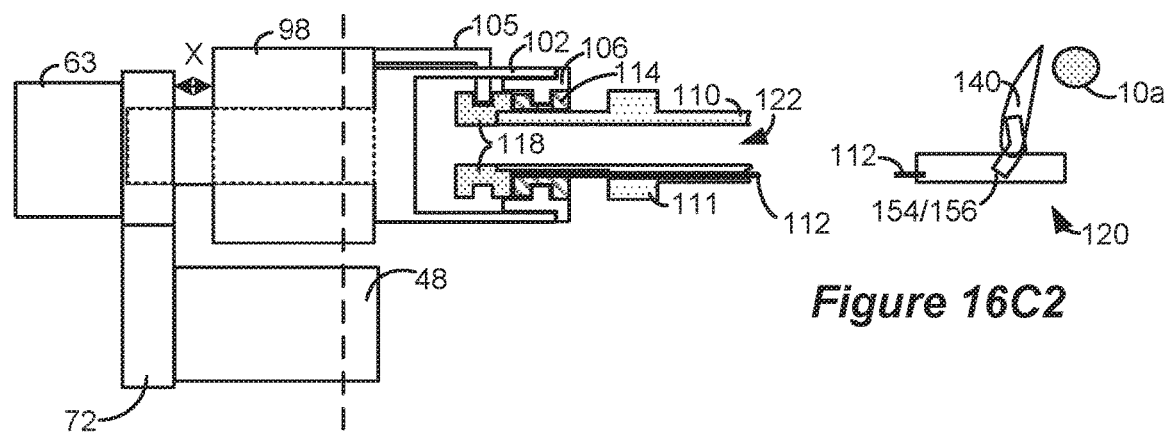
*Figure 16C2*
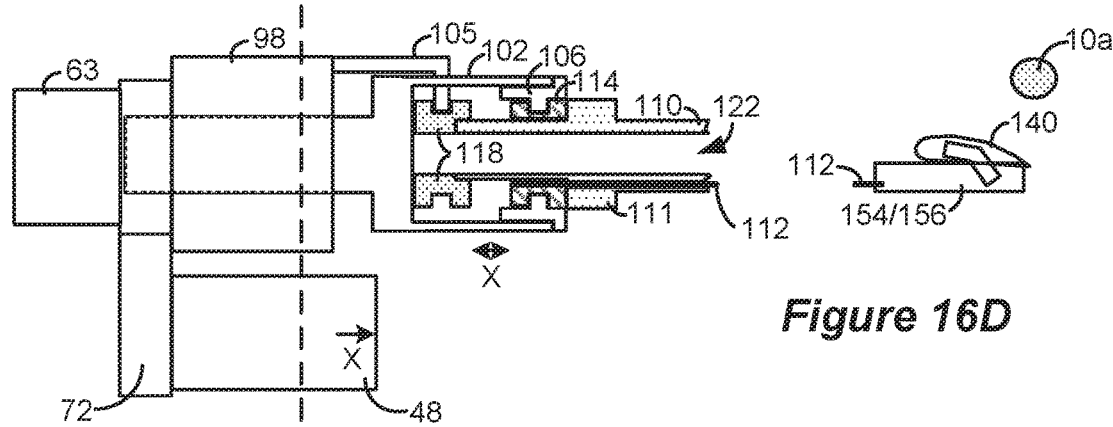
*Figure 16D*
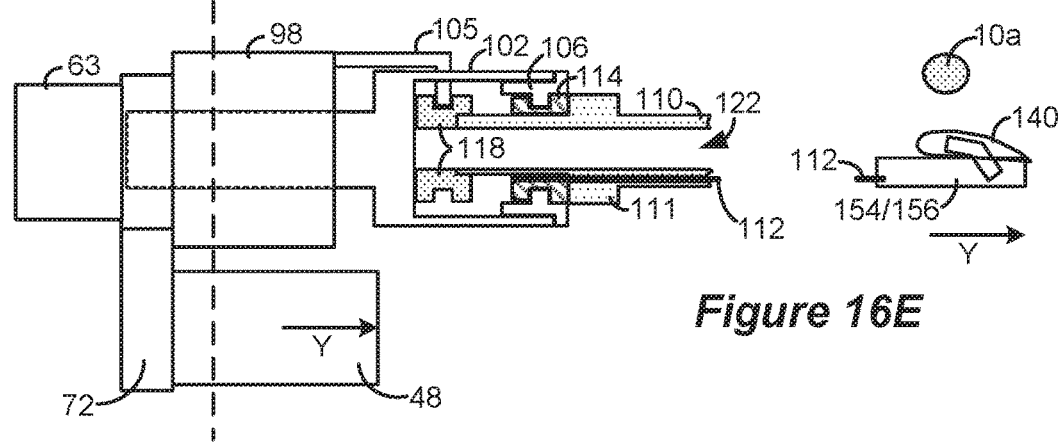
*Figure 16E*

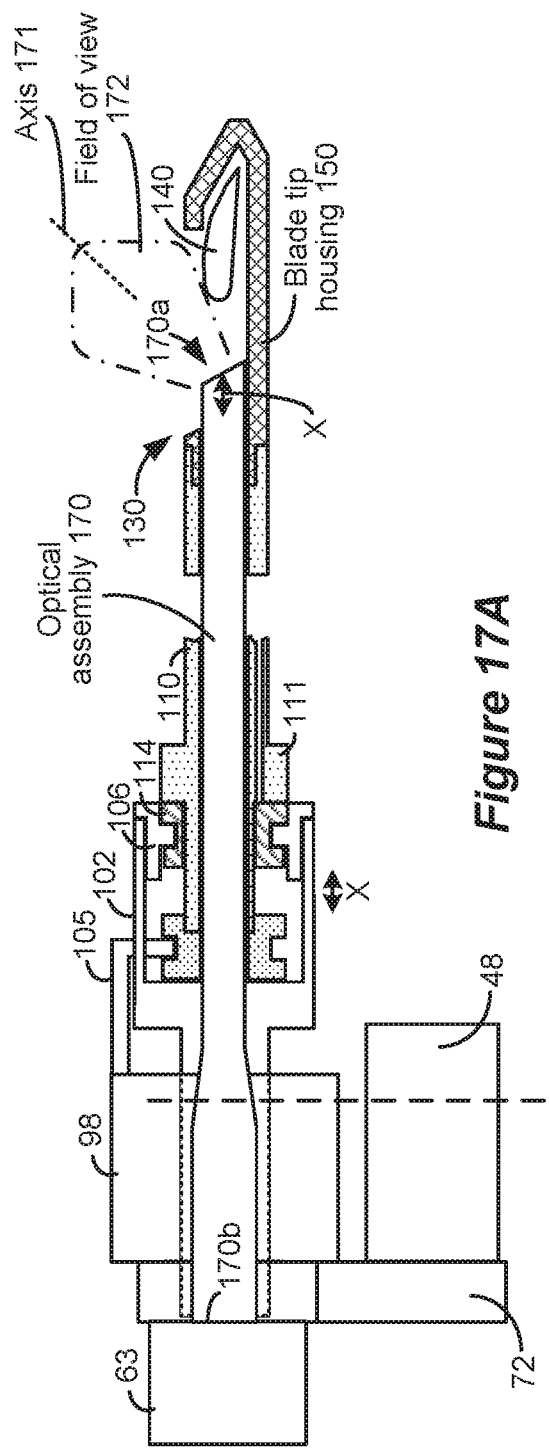
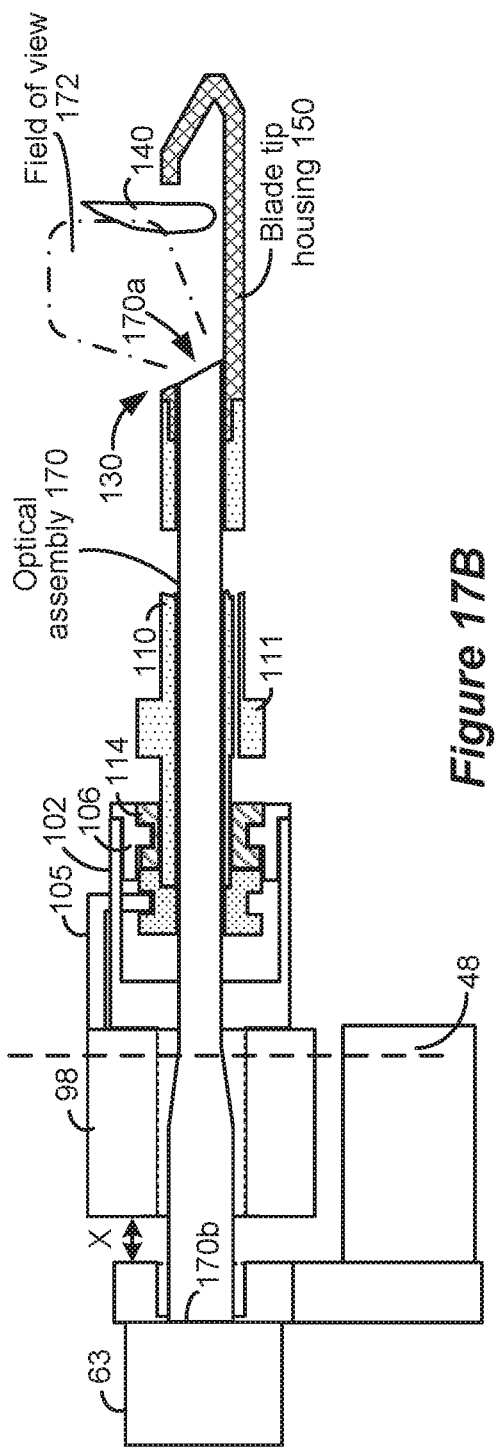
Figure 17A
Figure 17B

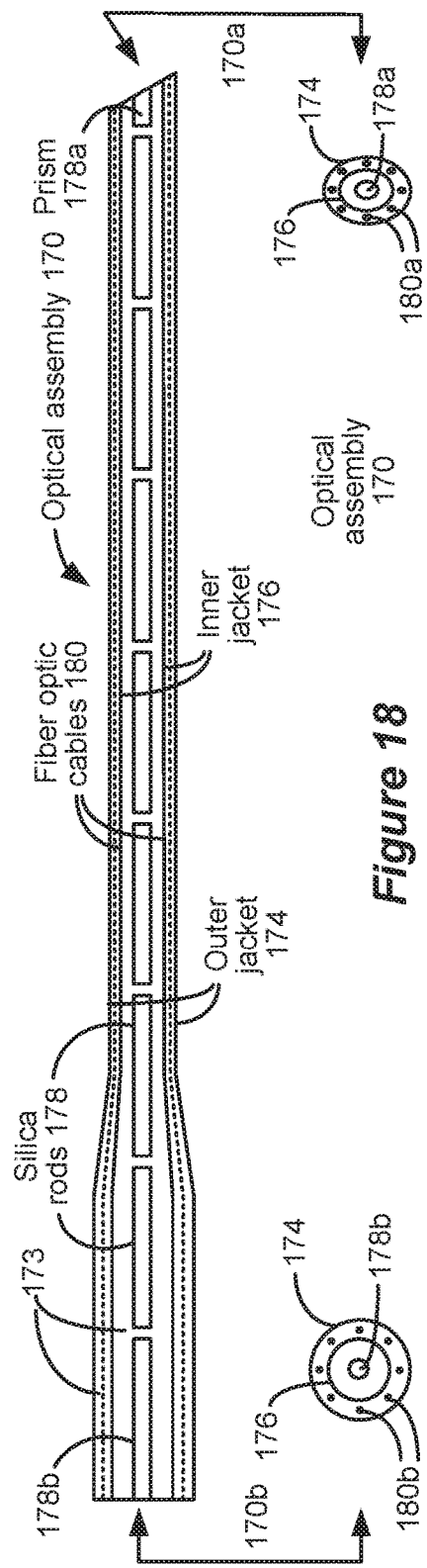
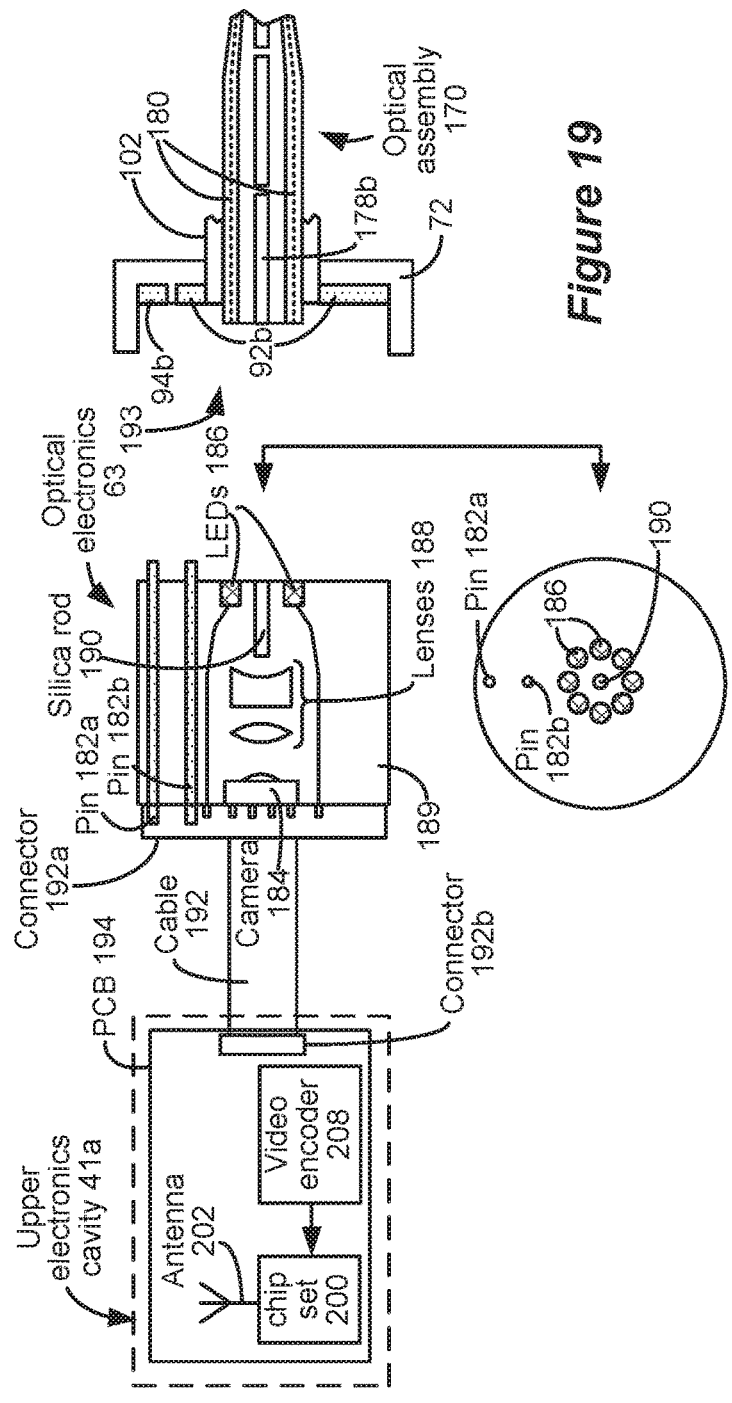
Figure 18
Figure 19

CARPAL TUNNEL RELEASE SURGICAL TOOL WITH WIRELESS VIDEO CAPABILITY

FIELD OF THE INVENTION

The present invention relates to a surgical tool for carpal tunnel release, and to methods of making and using the tool.

BACKGROUND

Carpal tunnel syndrome (CTS) is a medical condition caused by compression of the median nerve as it travels through the wrist at the carpal tunnel. CTS can cause pain, numbness, and tingling, typically in the thumb, index finger, middle finger, and the thumb side of the ring fingers. Weak grip strength and loss of manual dexterity may occur, and after a long period of time the muscles at the base of the thumb may atrophy.

While CTS can be treated using splints to limit wrist mobility, or with steroid injections, surgery can also be indicated. Such surgery is known as a carpal tunnel "release" (CTR) or "decompression" surgery, and is shown in FIG. 1A in a plane view and in FIG. 1B in a cross sectional view. The goal of CTR surgery is to incise the transverse carpal ligament 10 than spans across the base of the palm to alleviate pressure on the median nerve 12. CTR surgery can be performed "openly," essentially by slicing open the skin and fascia of the palm to reveal relevant structures, but FIGS. 1A and 1B shows an example of CTR as performed endoscopically.

In endoscopic CTR surgery, a small incision 14 is made near the base of palm, and a CTR tool 15 is inserted, which allows the surgeon to sever the transverse carpal ligament 10 with an incision 10a. CTR tool 15 can take many different forms, and is only generically described in FIGS. 1A and 1B. As shown, CTR tool 15 includes an internal portion (cannula) 18 that is insertable into the patient through incision 14, and an external portion 16 that operates as a handle for the surgeon. Sometimes incorporated in CTR tool 15 is an endoscope 19, which may comprise an instrument separate from the tool and useable in other contexts. In certain CTR tool designs, the endoscope may be positionable within the tool 15 and may include a light pipe that proceeds through the cannula 18 to allow the surgeon to view relevant anatomical structures to be cut. Commonly, the endoscope 19 includes a camera attachment (not shown) allowing the surgeon to view relevant anatomical structures on a display screen 22 coupled to the endoscope via a cable 20.

The external portion 16 further includes an activator 17 to release a blade 24 when the cannula 18 is in proper position relative to the transverse carpal ligament 10. Activator 17 can take many different forms and is only shown here for simplicity as a button on the external portion 16. When the blade 24 is released via the activator 17, it can be used to cut (10a) through the transverse carpal ligament 10 as shown via the image on the screen 22, and in the cross section of FIG. 1B. FIG. 1B also shows in cross section other anatomical structures such as various bones 28 of the hand and wrist, and various ligaments 26 coupled to the patient's fingers and thumb.

BRIEF DESCRIPTION OF THE DRAWINGS

FIGS. 9 through 11 show various internal components useful in extending and retracting a cannula and its blade tip assembly.

FIGS. 16A through 16E show details of how various portions of the extension and retraction mechanism move to extend and retract the cannula relative to the housing of the tool, and to extend and retract the blade relative to the blade tip assembly.

FIGS. 17A and 17B show an optical assembly within the tool, and how the assembly moves within the cannula.

FIG. 18 shows the optical assembly in cross section.

FIGS. 19 and 20 show how an optical electronics module can be coupled to the optical assembly to allow for tissue illumination, and to receive images of the patient tissue, without the use of wires or cables.

DETAILED DESCRIPTION

Figure 1:
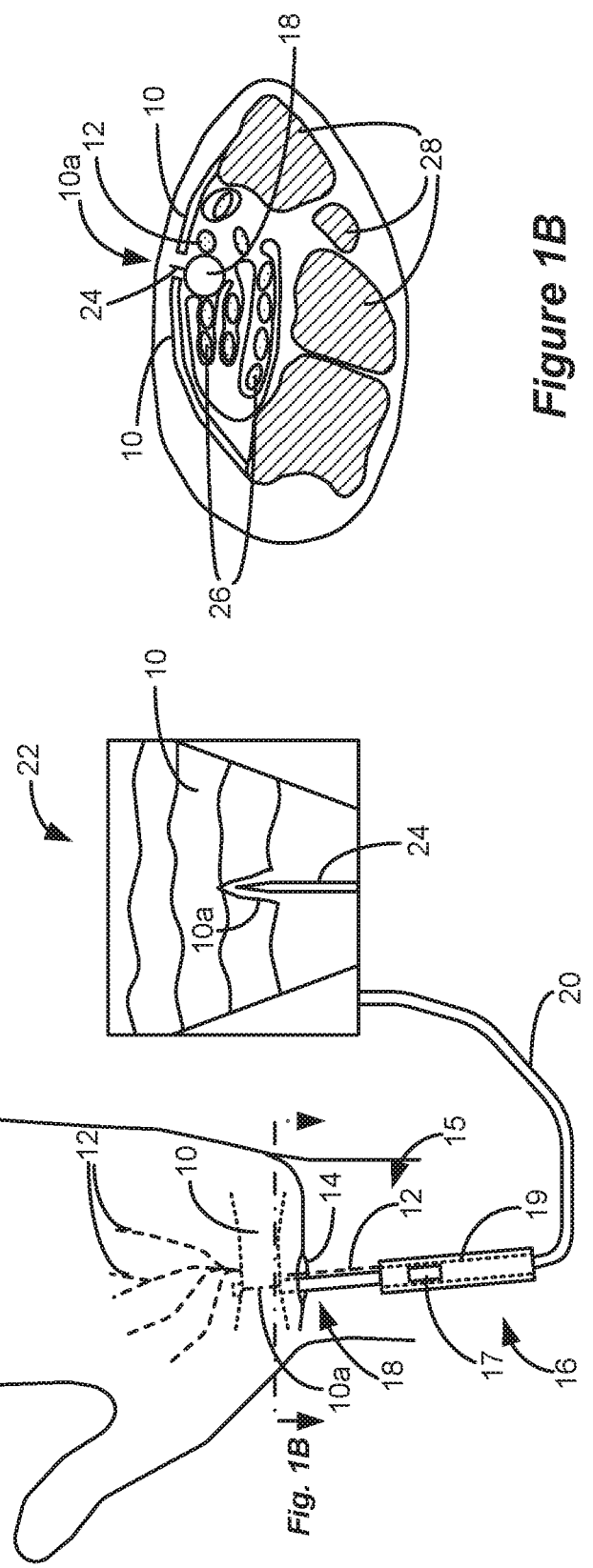
FIGS. 1A and 1B show an example of endoscopic Carpal Tunnel Release (CTR) surgery in accordance with the prior art.

The inventors believe that CTR tools such as 15 suffer from several drawbacks. First, to the extent that such tools include or incorporate the ability to view the structures being cut, such tools are cumbersome. They can require investment in a completely separate instrument—such as an endoscope 19—and therefore are not complete tool solutions. The endoscope 19 may require different components—such as an external video camera, an attachment to connect that camera to the endoscope, and an external light source to illuminate the patient's tissue—to be fully functional in a CTR surgical context. This makes such traditional CTR surgical solutions needlessly expensive and complicated. Further, and as shown in FIG. 1A, the endoscope 19 connects to a display screen 22 via a cable 20. This cable 20 is cumbersome for the surgeon, as it can get in the surgeon's, or surgical personnel's, way and can otherwise make it difficult to manipulate the tool in the patient.

Second, traditional CTR tools can have replacement parts that are expensive or difficult to replace. In particular, the blade 24 at the end of the cannula 18 may need replacing. Some traditional tools however require that the entire cannula 18 be replaced to replace the blade 24. This needlessly requires replacement of structures that are otherwise perfectly functional, which is wasteful and unnecessarily increases cost of use of the tool.

Third, traditional CTR tools can be difficult to clean and sterilize, or can have too many different components that need cleaning and sterilizing. For example, the CTR tool 15 and the endoscope 19, or their components, may each need to be cleaned separately, and the type of cleaning required may be different for different components, which adds complexity and again unnecessary cost. Further, at least certain portions of the CTR tool 15 or endoscope 19 may be formed of materials that do not permit them to be sterilized in an autoclave. An autoclave comprises a simple sterilization mechanism that uses steam at high temperatures and pressures to sterilize surgical equipment. However, many of the components in traditional CTR tools would be unable to handle the high pressures and temperatures that autoclaving provides. This is regrettable, because autoclaving is generally the cheapest and easiest alternative to more expensive sterilization techniques.

Fourth, the inventors see a need for a CTR tool whose simplicity will not require special resources and support. In some contexts, and depending on the type of tools and techniques used (e.g., open CTR surgery), it may be necessary to perform CTR surgery in an operating room (OR). This may require additional medical personnel to be present, such as one or more surgical nurses or anesthesiologists. In some circumstances, surgery may also require use of a post-surgery recovery room, and its related personnel, which again increases costs.

To address these shortcomings, the inventors have developed an improved CTR tool. The CTR tool is useable to perform CTR surgically endoscopically through a single incision in the patient, which as noted earlier is simpler than open CTR techniques that may require more-traditional and more-expensive surgical resources and support. The CTR tool however lacks a traditional, self-standing endoscope (such as 19, FIG. 1A), and instead includes all dedicated optical components—including light emitters (e.g., LEDs) and a camera—within the housing of the tool. Preferably, the tool includes wireless communication means—such as a Bluetooth antenna and chip set—to broadcast video images from the camera to an external display in real time to allow the surgeon to see the patient's anatomy, and in particular the transverse carpal ligament to be cut. Because optics in the tool are handled wirelessly, the tool lacks a cable (compare 20, FIG. 1A), and is thus more convenient to use. The tool also includes a battery for operational power, i.e., to power the optical components and the wireless transfer of the video images.

As will be shown in the figures that follow, the improved CTR tool is also modular, thus allowing different portions of the tool to be replaced if necessary. For example, the cannula includes a blade tip assembly that can be easily replaced after each use of the tool, while leaving otherwise functional portions of the cannula in place. Other aspects of the improved CTR tool can also be easily changed, including (less frequently) its battery and an optical electronics module that may include both the LEDs required for illumination of tissue and the camera used to capture images from the patient. These replaceable portions are simpler and significantly cheaper to replace than in traditional CTR tools, and allow still-functioning portions of the tool to remain unreplaced, which lower costs associated with use of the tool.

Finally, the improved CTR tool is comprised of components manufactured of materials that can be cleaned and sterilized using an autoclave alone. This is significant as it allows the tool to be more easily and cheaply used in subsequent surgeries. This also encourages use of the CTR system in non-traditional contexts, such as minor surgical facilities or facilities that might be more remote and which might otherwise lack the resources and support traditionally necessary for surgery. The CTR system may simply comprise of the tool (and its replacement parts), a monitor (such as a computer, television, or tablet, having wireless display capability), and an autoclave. Use of the CTR tool within such a system is expected to greatly improve the throughput with which, and to reduce the per-patient cost at which, CTR surgery can be performed.

Figure 2:
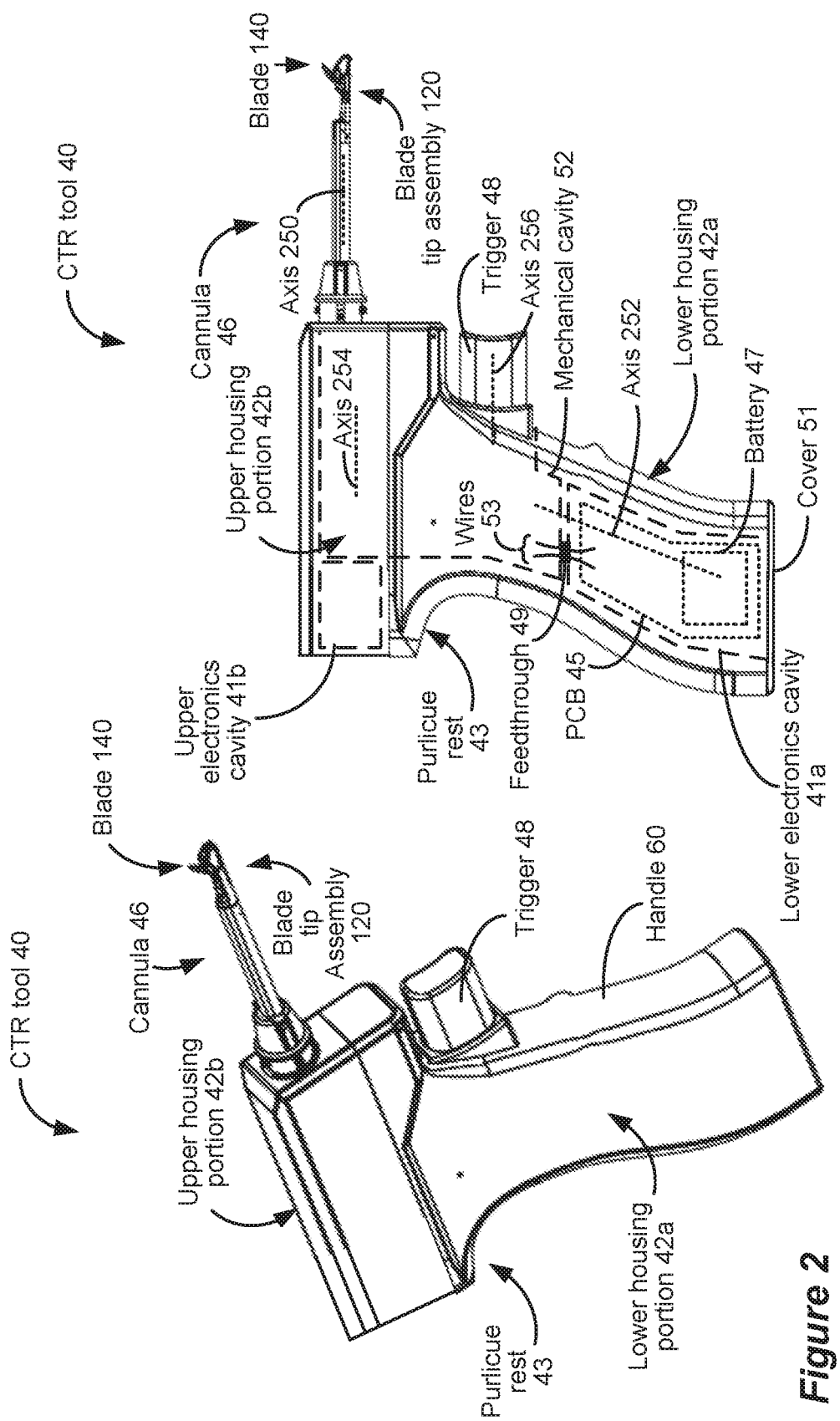
FIG. 2 shows an example of a CTR tool in accordance with the invention, which tool is wireless, cableless, and battery powered.

A first view of the improved CRT tool 40 is shown in FIG. 2 in perspective and side views. The tool 40 is formed of a lower housing portion 42a and an upper housing portion 42b, and includes a cannula 46 emanating from the upper housing portion 42b. As explained in detail later, the end of the cannula 46 includes a blade tip assembly 120 including a retractable blade 140. Although not yet shown in FIG. 2, the blade tip assembly 120 also includes an optical window (130, FIG. 11) proximate to the blade 140 through which the patient's anatomy can be illuminated and viewed. The tool 40 is generally shaped like a handgun, with lower housing portion 42a including a handle 60 that can be grasped by the surgeon. A purlicue rest 43 is formed at the back of the lower housing portion 42a to allow the tool to rest on the surgeon's purlicue (the portion of the hand between the thumb and index finger) when grasped by the surgeon. The lower housing portion 42a includes an opening 58 (FIG. 4) through which a trigger 48 protrudes and can be manipulated by the surgeon's index finger. As will be explained later, pulling the trigger 48 acts to both extend and retract the blade 140 from the blade tip assembly 120 and to extend and retract the cannula 46 from and to the upper housing portion 42b to allow the blade to cut the patient's tissue (e.g., the transverse carpal ligament 10). In other words, the surgeon will be able to cut the tissue without retracting the CRT tool 40 relative to the patient (i.e., pulling the tool away from the patient), which minimizes the possibility of an unexpected error.

The cannula 46 has a long axis 250, and the upper housing portion 42b has a long axis 254 parallel with axis 250. The trigger 48 is depressable along an axis 256 with is parallel to axis 250 along which the cannula 46 can move, as explained further below. The lower housing portion 42a also has a long axis 252 which, due to the "gun shaped" nature of the tool 40, is not necessarily parallel to axis 250. Instead, axis 252 may be said to be substantially perpendicular to axis 250, which may be broadly defined as being between 60 to 120 degrees relative to the long axis 250. In other designs, axis 252 can be parallel with axis 250.

Figure 21:
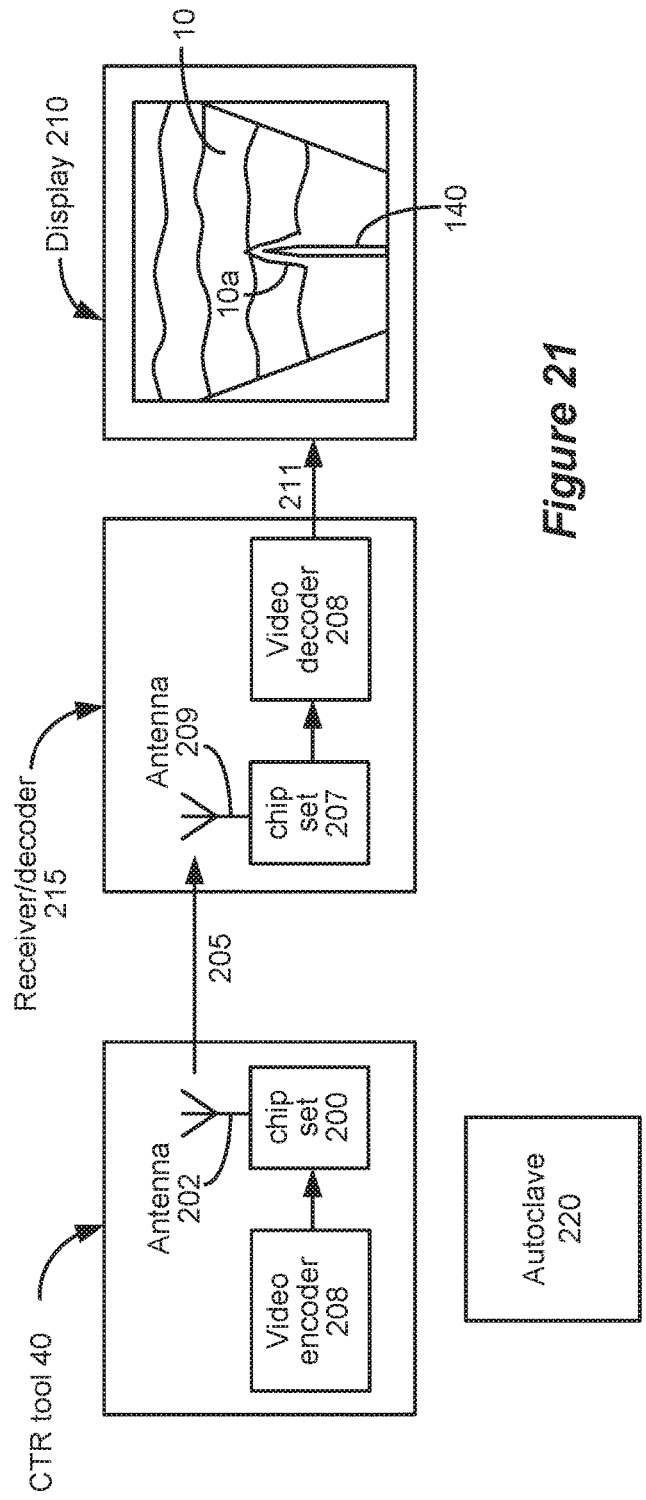
FIG. 21 shows aspects useable in a CRT system, including a display capable of wirelessly receiving images of the patient's tissue from the tool, and an autoclave useable to sterilize the tool and its components.

As shown in the side view of FIG. 2, the tool 40 preferably has one or more internal cavities containing various mechanical and electrical components. A mechanical cavity 52 houses an internal actuator 50 (FIGS. 3 and 5), with cavity 52 spanning both the lower and upper housing portions 42a and 42b. An upper electronics cavity 41b can be formed inside the upper housing portion 42b, and as will be described later, can include supporting electronics for the tool, such as a wireless chip set 200 and antenna 202 (FIG. 21). A lower electronics cavity 41a in the lower housing portion 42a can include a printed circuit board 45 and battery 47 to provide operational power for the tool. The bottom of the lower housing portion 42a can include a removable hermetic cover 51, thus allowing a user to gain access to, and if necessary replace, the battery 47. The battery 47 can be rechargeable or non-rechargeable. Although not shown, the lower housing portion 42a or cover 51 can include external contacts or a port allowing the battery to be recharged if it is rechargeable. While two separate electronics cavities 41a and 41b are shown, this is not strictly necessary, and relevant electronic components in the system could be placed in either cavity, or in a single cavity in different designs.

Figure 3:
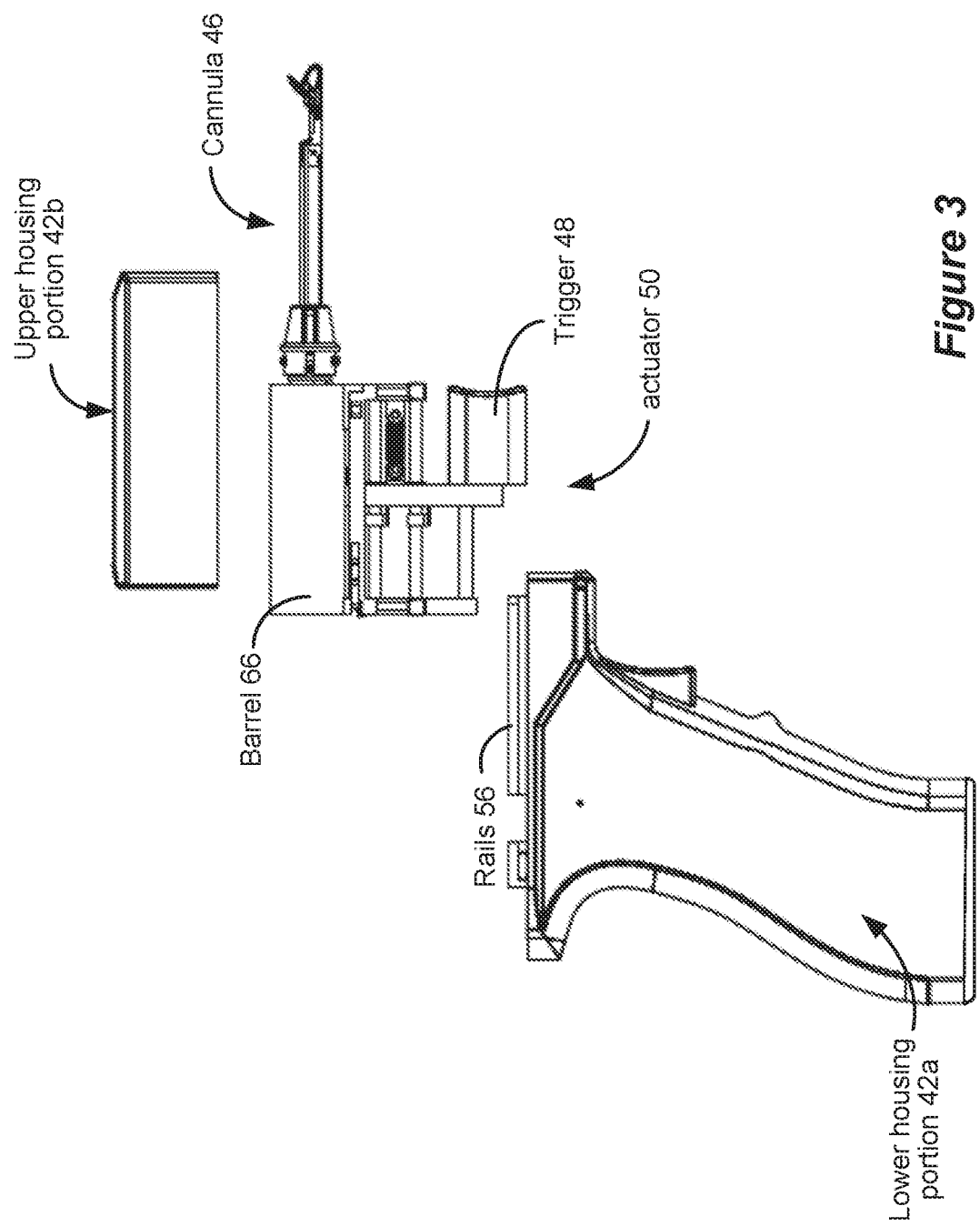
FIGS. 3 through 7 show various external and internal aspect of the tool, including an extension and retraction mechanism.

FIG. 3 shows the upper housing portion 42b removed from the lower housing portion 42a, and shows the actuator 50 within mechanical cavity 52. The mechanical cavity 52 in the upper housing portion 42b encloses a barrel 66 through which various internal components slide when the cannula 46 is both retracted into and extended from the upper housing portion. Other aspects of the actuator 50 explained later fit into the mechanical cavity 52 in the lower housing portion 42a.

Figure 4:
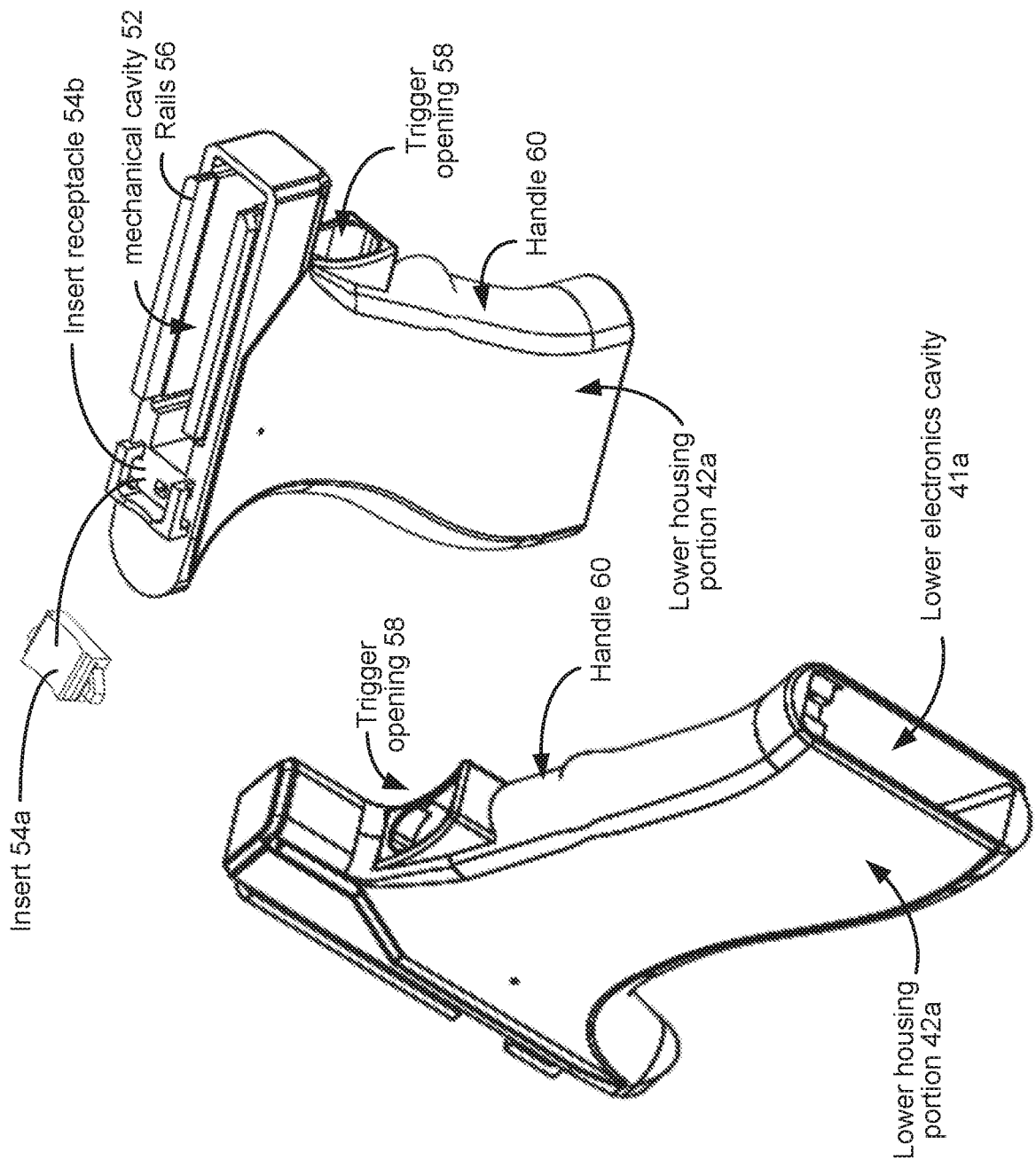

FIG. 4 shows top and bottom views of the lower housing portion 42a in isolation with the upper housing portion 42b removed. From these perspectives, the lower electronic cavity 41a and part of the mechanical cavity 52 can be seen. Further shown are rails 56 which meet with corresponding rails on the upper housing portion 42b (not shown). Rails allows the upper housing portion 42b to be connected to the lower housing portion 42a by sliding the upper housing portion into position until it locks. As shown, the top of the lower housing portion 42a includes an insert receptacle 54b into which an insert 54a can be fit. This insert 54a can be used to support aspects that slide within the upper housing portion 42b as the cannula 46 is retracted and extended into and from the tool, and in particular can be used to support the optical electronics 63 (FIG. 6) as it moves.

Figure 5:
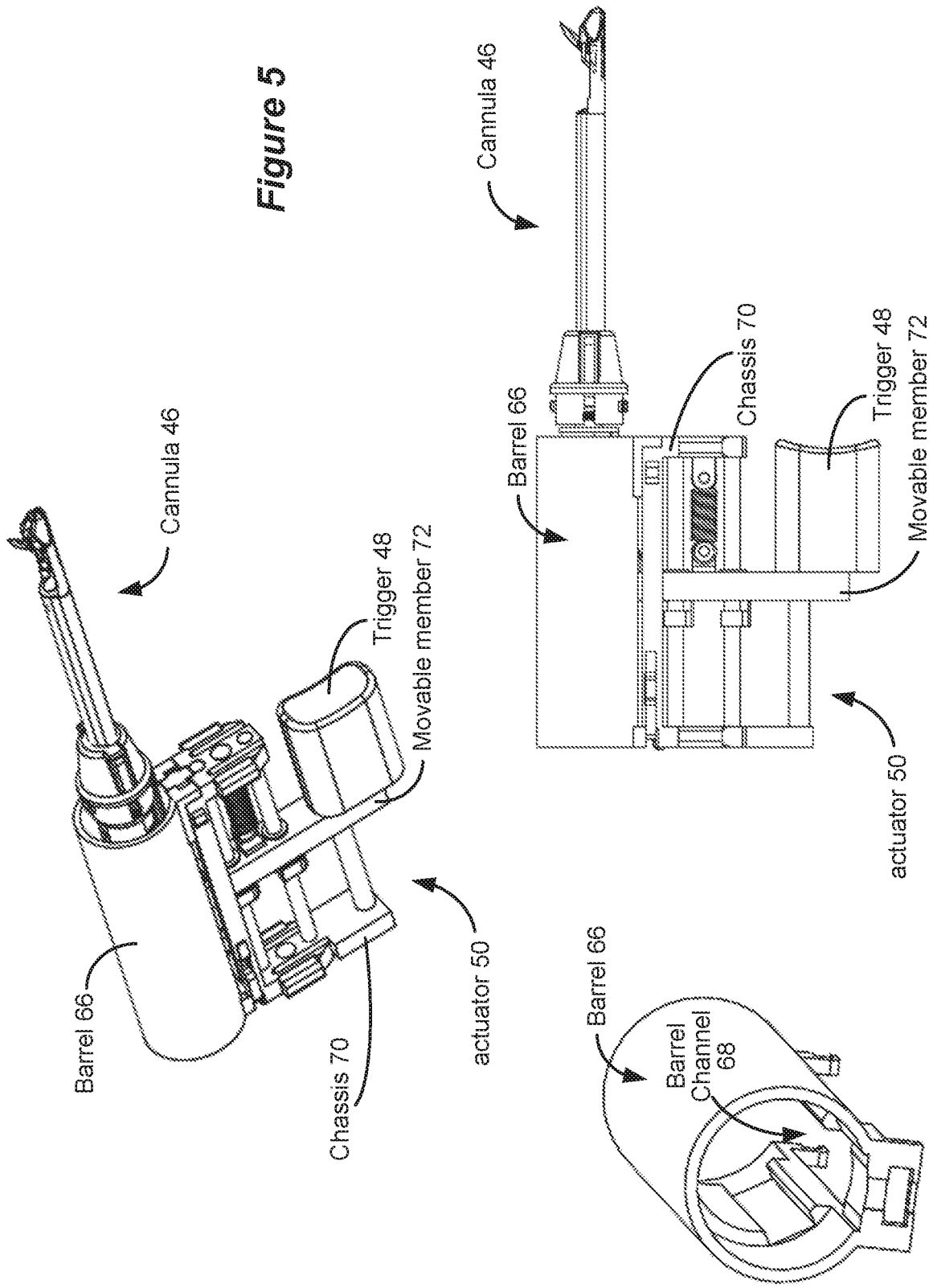
Figure 7:
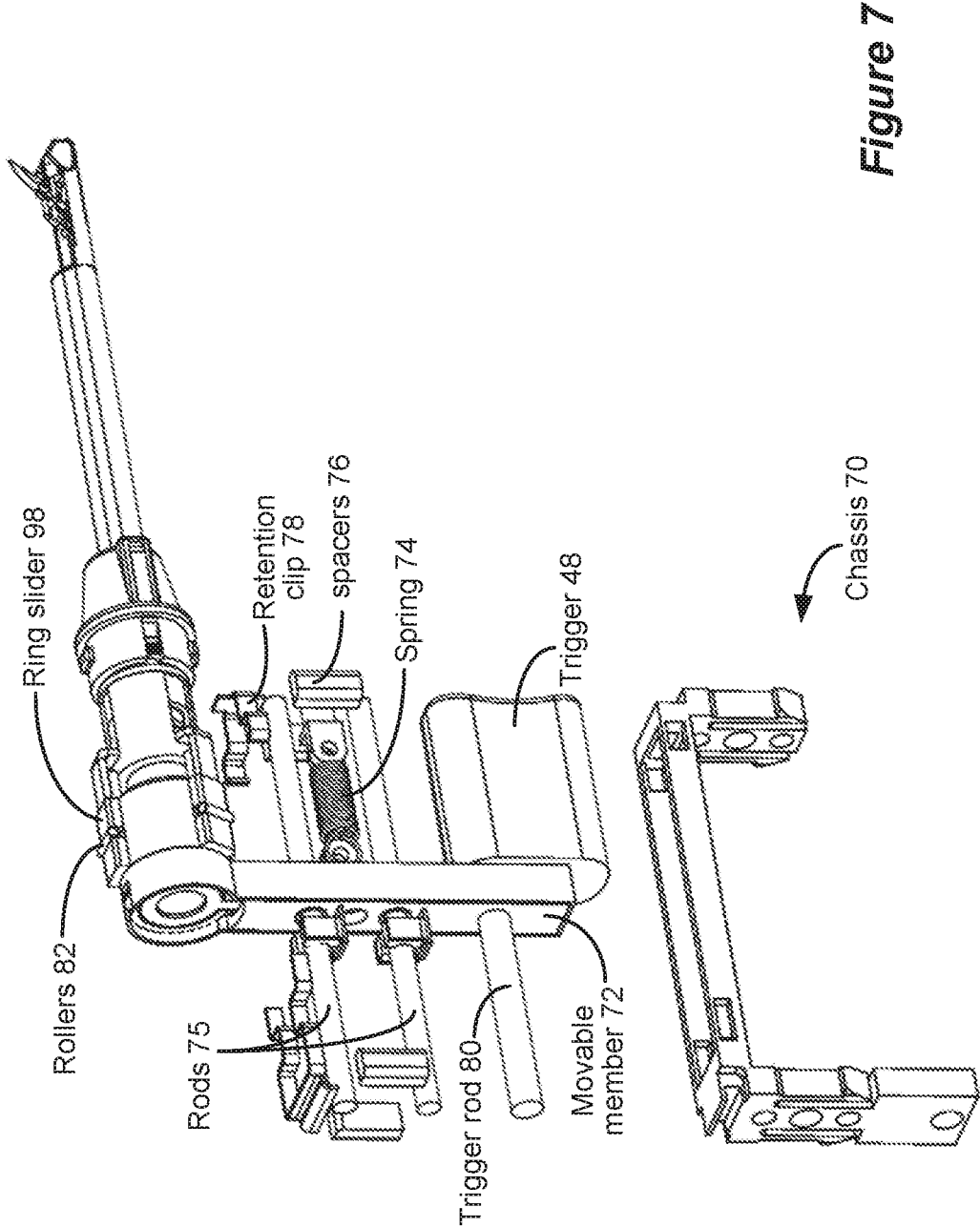

FIG. 5 shows the actuator 50 in isolation from different views. Manufacture of the actuator 50 centers around a chassis 70, which is shown in isolation in FIG. 7. The chassis 70 is held in place within the lower housing portion 42a by retention clips 78 which can also support spacers 76. The retention clips 78 largely prevent the chassis 70 from moving horizontally within the lower housing portion, while the spacers prohibit vertical movement. The chassis 70 may also be held in place using pins (not shown) passing though the lower housing portion 42a. Returning to FIG. 5, the barrel 66 can be seen in isolation, and includes a barrel channel 68 or slot at its bottom through which a movable member 72 can pass from the mechanical cavity 52 in the lower housing portion 42a. The barrel 66 does not slide within the upper housing portion 42b, and instead is affixed to the lower housing portion 42a and/or the retention clips 78.

Figure 6:
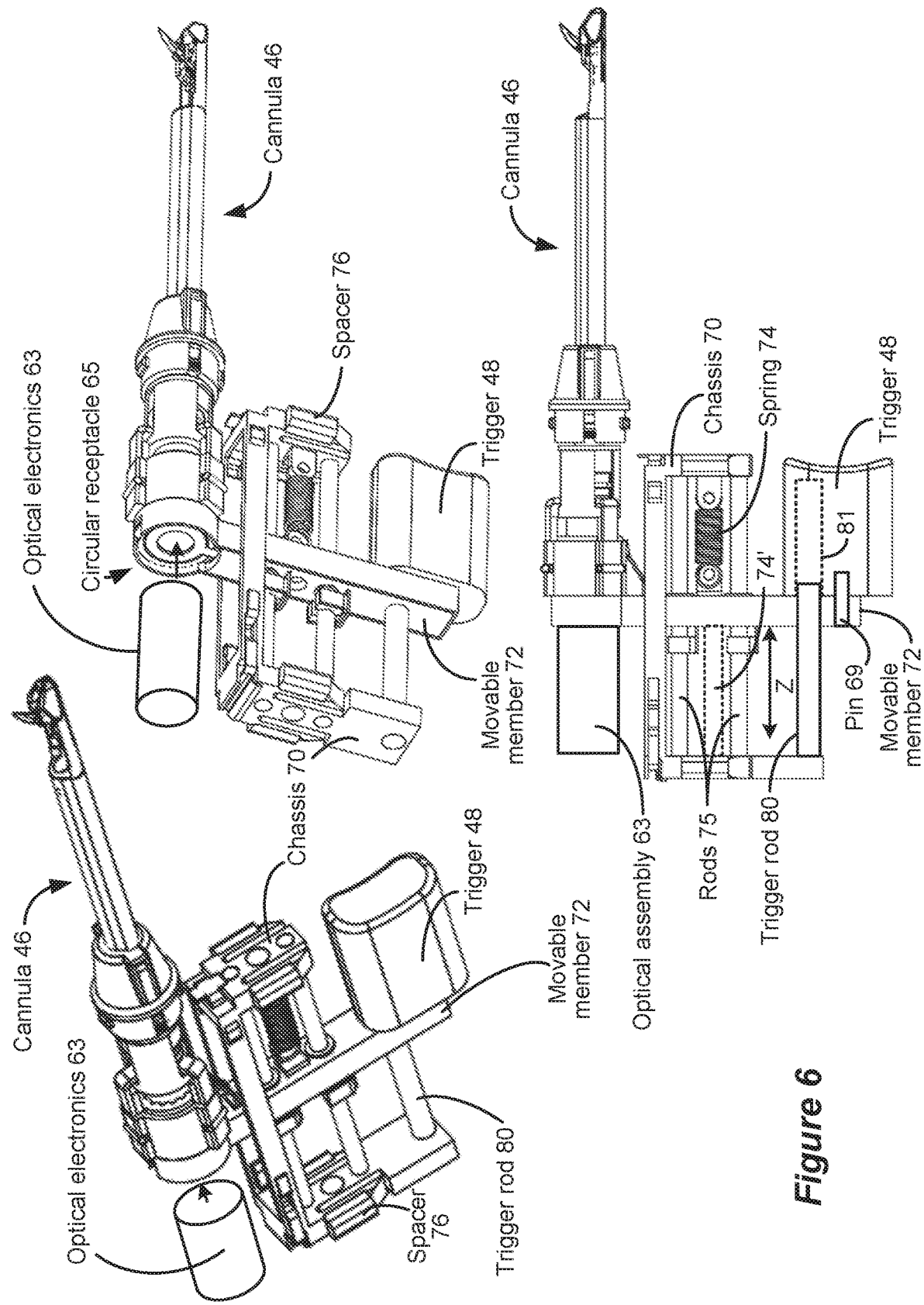

FIG. 6 shows further details of the actuator 50 with the barrel 66 removed so that its internal components can be seen. The movable member 72 just mentioned is coupled to the trigger 48, such that the movable member 72 slides through distance Z as the trigger 48 is pushed. To help support such movement, a trigger rod 80 is affixed to a left vertical wall of the chassis 70 and passes through a hole 77 (FIG. 8) in the movable member 72 and a recess 81 (FIG. 6) in the trigger 48, such that movement of the movable member 72 stops when an end of the trigger rod 80 meets with an end of the recess 81 (i.e., when the trigger 48 is fully pressed in). The trigger 48 may be rigidly affixed to the moveable member 72 using a pin 69 or other securing means.

An extension spring 74 coupled to the movable member 72 and a right vertical wall of the chassis 70 biases the movable member 72, and keeps the trigger 48 in its outmost position (to the right as shown) when it is not pressed. Also helping to support movement of the movable member 72 are rods 75, which are fixed at both ends to the vertical walls of the chassis 70, and pass through holes (similar to 77, but not shown) in the movable member 72. Thus, when the trigger 48 is pressed, the movable member 72 slides horizontally over both the trigger rod 80 and the rods 75. Other means of biasing the trigger 48 can be used. For example, a compression spring 74' may be placed between the moveable member 72 and the left vertical wall of the chassis 70 that biases the trigger outward to the right. Leaf springs (not shown) may also be used between the moveable member 72 and the left vertical wall of the chassis. In short, there are many different ways to bias the trigger 48, and more than one of these means may be used in conjunction with each other.

In FIG. 6, an optical electronics module 63 is shown which is attached to a circular receptacle 65 of the movable member 72. As will be discussed later, this module 63 includes electronics necessary for illumination of the patient's tissue, and includes a camera to capture images of the illuminated tissue. The optical electronics module 63 slides inside of the upper housing portion 42b (within the barrel 66) as the movable member 72 slides, along with other components, as explain further later.

Figure 8:
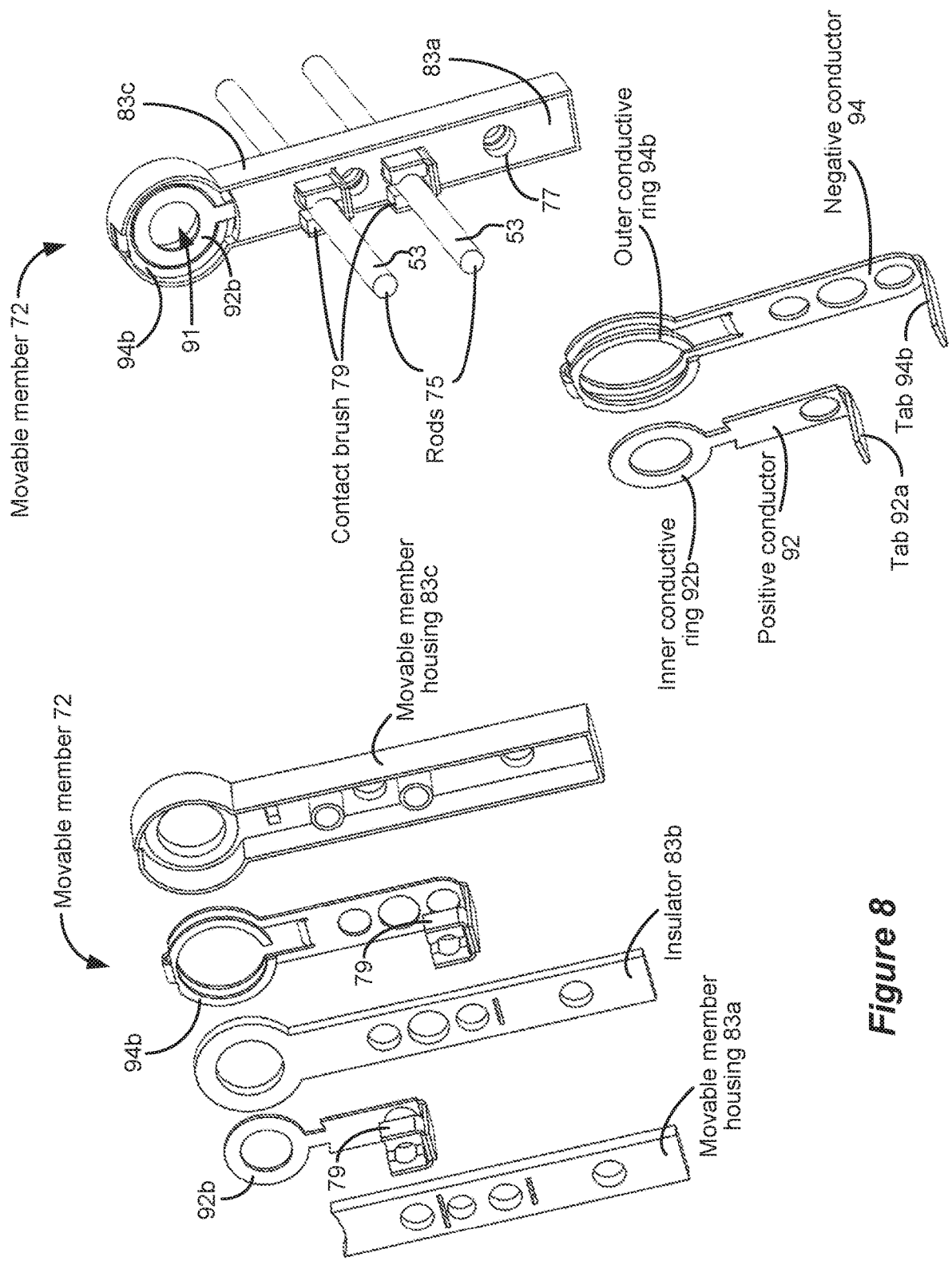
FIG. 8 shows aspects of a moveable member in the extension and retraction, which includes conductive elements for providing power to various portions of the tool.

FIG. 8 shows construction of the movable member 72. In one example, the movable member 72 is preferably used to provide power to the optical electronics module 63 and other component of the system that may reside in upper electronics cavity 41b (FIG. 2). The movable member 72 in this example includes two non-conductive outer housings 83a and 83c. Within these housings are a positive conductor 92 and a negative conductor 94 (or vice versa), which are separated and insulated from each by an insulator 83b. The conductors 92 and 94 are bent to form tabs 92a and 94a respectively. Conductive contact brushes 79 can be placed on the tabs, such that the rods 85 are in contact with, but can slide through, the contact brushes 79. In one example, the rods 75 may be conductive (e.g., graphite), and used as conductors to route power as well as to provide mechanical support to the movable member 72. In this regard, wires 53 can be connected to the conductive rods 75 in various fashions. As shown in FIG. 2, such wires 53 can emanate from the lower electronic cavity 41a, and in particular can be used to carry a positive and negative power supply voltage (i.e., the positive and negative voltages of the battery 47, perhaps as regulated) to the conductive rods 75. Such wires can proceed from the lower electronics cavity 41a via a feedthrough 49, which can be hermetically sealed to separate the lower electronics cavity from the mechanical cavity 52 if desired.

Once the wires 53 are connected to the conductive rods 75 as shown in FIG. 8, they can conduct through the contact brushes 79 and the tabs 92a and 94a to the positive conductor 92 and the negative conductor 94. These conductors terminate at rings 92b and 94b at the top of the movable member 72. Preferably, conductor 94 is bent at the top around the insulator 83b so that its corresponding ring 94b resides in the same vertical plane as the does ring 92b. This is accomplished by forming ring 94b with a larger diameter than ring 92b, which allows concentric rings 92b and 94 to lie in the same plane without shorting. The rings 92b and 94b are exposed so that they can make electrical contact with the optical electronics module 63 (FIG. 6) when that module 63 is connected to the movable member 72. Further details of how mechanical and electrical coupling occurs between the movable member 72 and module 63 are explained later with reference to FIGS. 19 and 20. To summarize, power and ground can be provided by the battery 47 in lower electronics cavity 41a to the optical electronics module 63 and other system components in the upper electronics cavity 42b via the positive and negative rings 92b and 94b of the movable member 72. As will be seen later, the rings 92b and 94b operate similar to a slip ring assembly that allow for power to be transmitted to the cylindrical optical electronics module 63 even if that module rotates around the long axis of the cannula.

Note that it is not strictly required that the rods 75 be conductive and used in this process of routing power. Instead, rods 75 may be non-conductive, in which case the wires 53 could be connected directly to the contacts brushes 79 or to the tabs 92a and 92b, or can be connected to the conductors 92 and 94 in other fashions. Note that because the movable member 72 is designed to move within the mechanical cavity, wires 53 are preferably provided with sufficient slack such that they can stay connected to the movable member 72 through its full range of movement.

Figure 9:
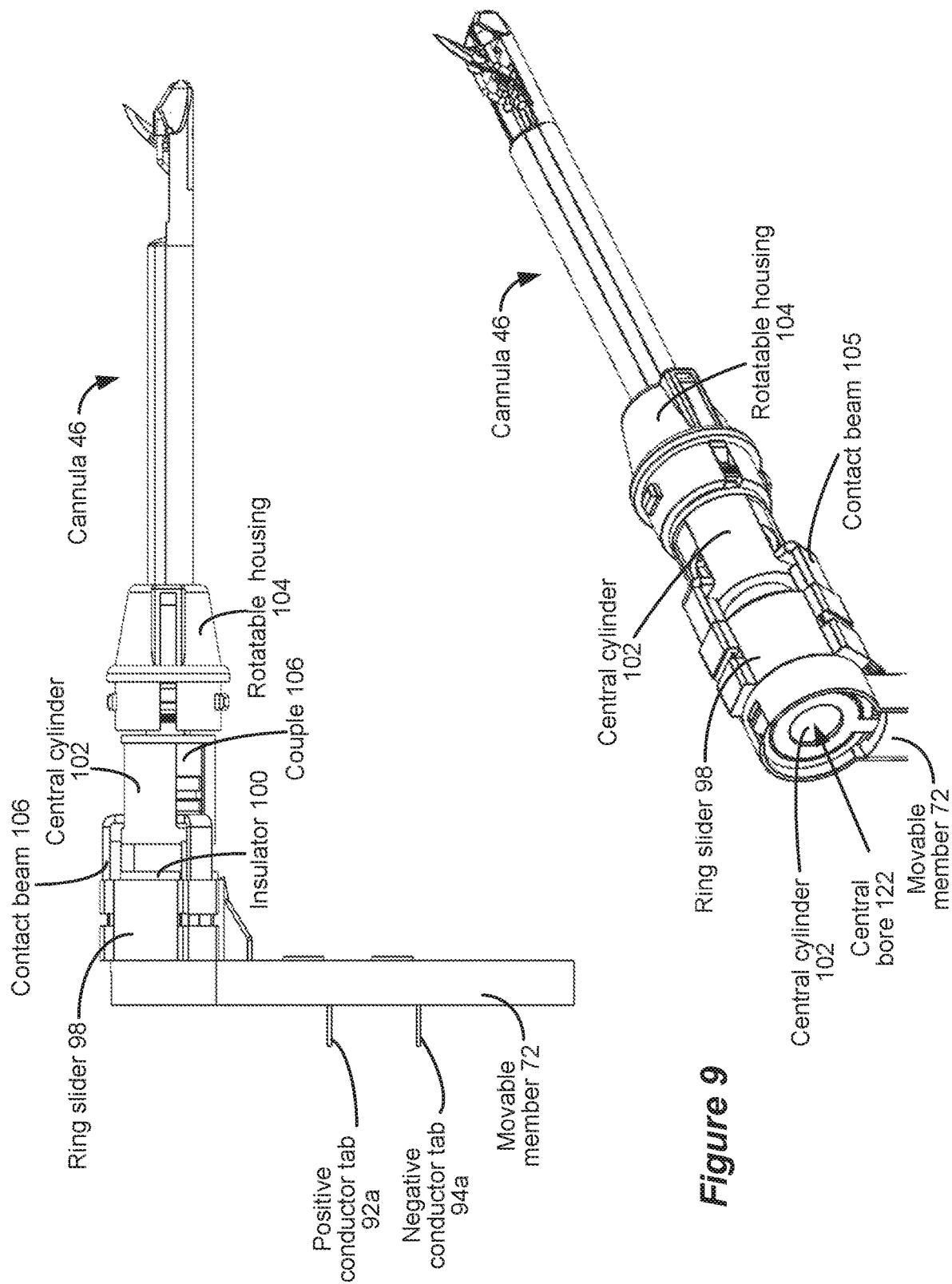
Figure 10:
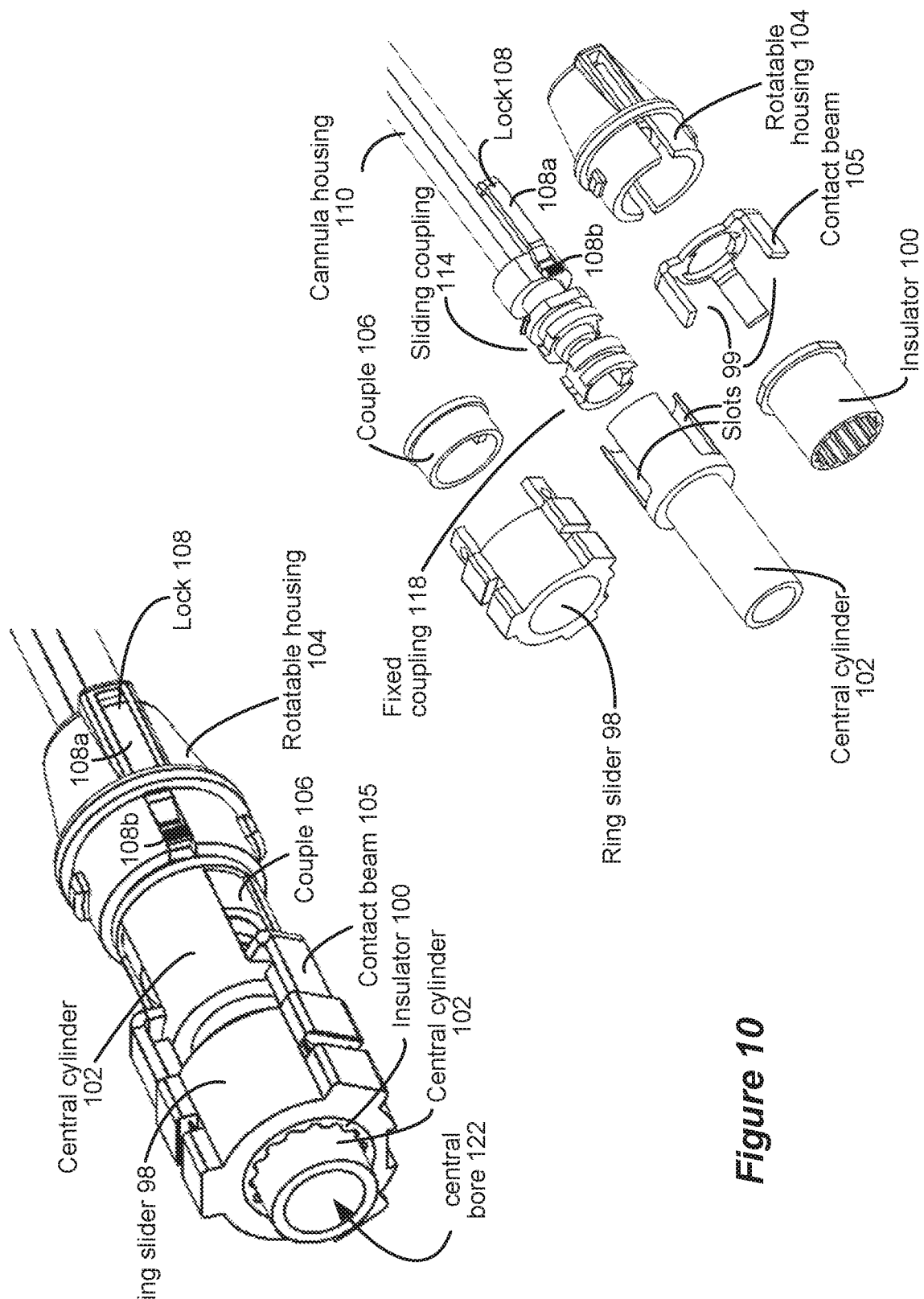

As noted earlier, pulling the trigger 48 horizontally moves the movable member 72, which acts both to retract and extend the cannula 46 and to retract and extend the blade 140 of the blade tip assembly 120. Components that promote these various movements within the tool 40 are shown in further detail starting with FIGS. 9 and 10. FIG. 10 shows further details of these and other components with the movable member 72 removed for easier viewing, and shows the various components in an exploded view so that their shapes can be better appreciated.

A ring slider 98 slides horizontally through the barrel 66 (FIG. 5), and in one example can include notches to accommodate for one or more rollers 82 (FIG. 7) around its circumference to promote smooth movement along a long axis through the cannula 46. The ring slider 98 may also be dimensioned to simply smoothly slide within the barrel 66 with the need of rollers. Also present is a central cylinder 102. As will be described in further detail later, the central cylinder 102 has an end which is press fit (or glued, sonic soldered, etc.) within a hole 91 (FIG. 8) of the movable member 72, and thus slides as the member 72 moves. Note from FIG. 8 that this hole 91 can be formed in the middle of the inner and outer conductive rings 92b and 94b of the movable member, although the central cylinder 102 may also be coupled to the movable member 72 in different ways. Press fit (or glued, sonic soldered, etc.) within the other end of the central cylinder 102 is a couple 106 which connects to a sliding coupling 114, as explained later with reference to FIG. 11. A contact beam 105 is fixed to the ring slider 98, and is coupled to a fixed coupling 118, again explained with reference to FIG. 11. Notice that the central cylinder 102 and contact beam 105 are formed with interleaved slots 99 (three, at 120 degree around their circumferences), thus allowing these components to horizontally move with respect to each other without interference.

As best shown in FIG. 10, the cannula housing 110 includes a rotatable housing 104 which includes one or more locks 108. The rotatable housing 104 allows the surgeon to rotate the cannula housing 110 around its long axis at a position that is most comfortable for the surgeon, which rotating will also change the rotational angle at which a patient's tissue can be viewed and cut. Axial rotation is promoted or prohibited by the locks 108. Preferably there are two such locks 108 spaced at 180 degrees around the rotatable tip 104 (only one is shown). The locks 108 are affixed in the rotatable housing 104 in a manner that allows them to bend inward towards the long axis of the cannula when pressed at surfaces 108a. So pressing these surfaces 108a will move contact surfaces 108b inward as well. These contacts surfaces 108b are normally in contact with the upper housing portion 42b (FIG. 3), and so are normally locked when not pressed to prevent the rotatable housing 104 from rotating. When the locks 108 are pressed at surfaces 108a, the surfaces 108b move inward allowing rotational movement.

Also relevant to rotation movement is an optional insulator 100, which is press fit (or glued, sonic soldered, etc.) within the ring slider 98, and which receives the central cylinder 102 therethrough. As can be seen, the inner diameter of the insulator 100 is ribbed where it contacts the outer diameter of the central cylinder 102. The ribbed inner surface of the insulator 100 allows the central cylinder 102 to pass relatively smoothly horizontally through the ring slider 98, but provides some resistance if the cannula housing 110 is rotated using the rotatable housing 104 (i.e., when the locks 108 are pressed). To summarize, the insulator 100, the rotatable housing 104 and the locks 108 allow the surgeon to radially turn the cannula 46 with some force to change the radial angle at which the tissue can be viewed and cut, and to lock a particular angle into place. In this regard, and jumping ahead, note that an optical assembly 170 (FIGS. 17 and 18) will be placed in a center bore 122 at the center of the various components and the cannula housing 110.

FIG. 11 shows the housing 110 of the cannula 46, including components that interface with the components just discussed. The cannula housing 110 includes a shoulder 111, and includes a fixed coupling 118 which is press fit (or glued, sonic soldered, etc.) onto and affixed to the housing 110. Between the fixed coupling 118 and the shoulder 111 is a sliding coupling 114, which is free to slide along the housing 110 between the fixed coupling 118 and the shoulder 111. Both the couplings 114 and 118 have grooves on their outer diameters. The groove on the sliding coupling 114 meets with a protrusion on the couple 106, which is in turn press fit (or glued, sonic soldered, etc.) and affixed with the central cylinder 102. The groove on the fixed coupling 118 meets with a contact beam 105, which is in turn press fit (or glued, sonic soldered, etc.) onto and affixed to the ring slider 98.

The sliding coupling 114 is connected to a wire 112 which proceeds slidably through a wire channel 113 in the cannula housing 110. This wire 112 is connected at its other end to a mechanism in the blade tip assembly 120, which acts to retract or extend the blade 140 as the sliding coupling 114 moves between the shoulder 111 and the fixed coupling 118. Before explaining this movement in further detail, the attachment, construction, and operation of the blade tip assembly 120 is discussed.

Figure 12:
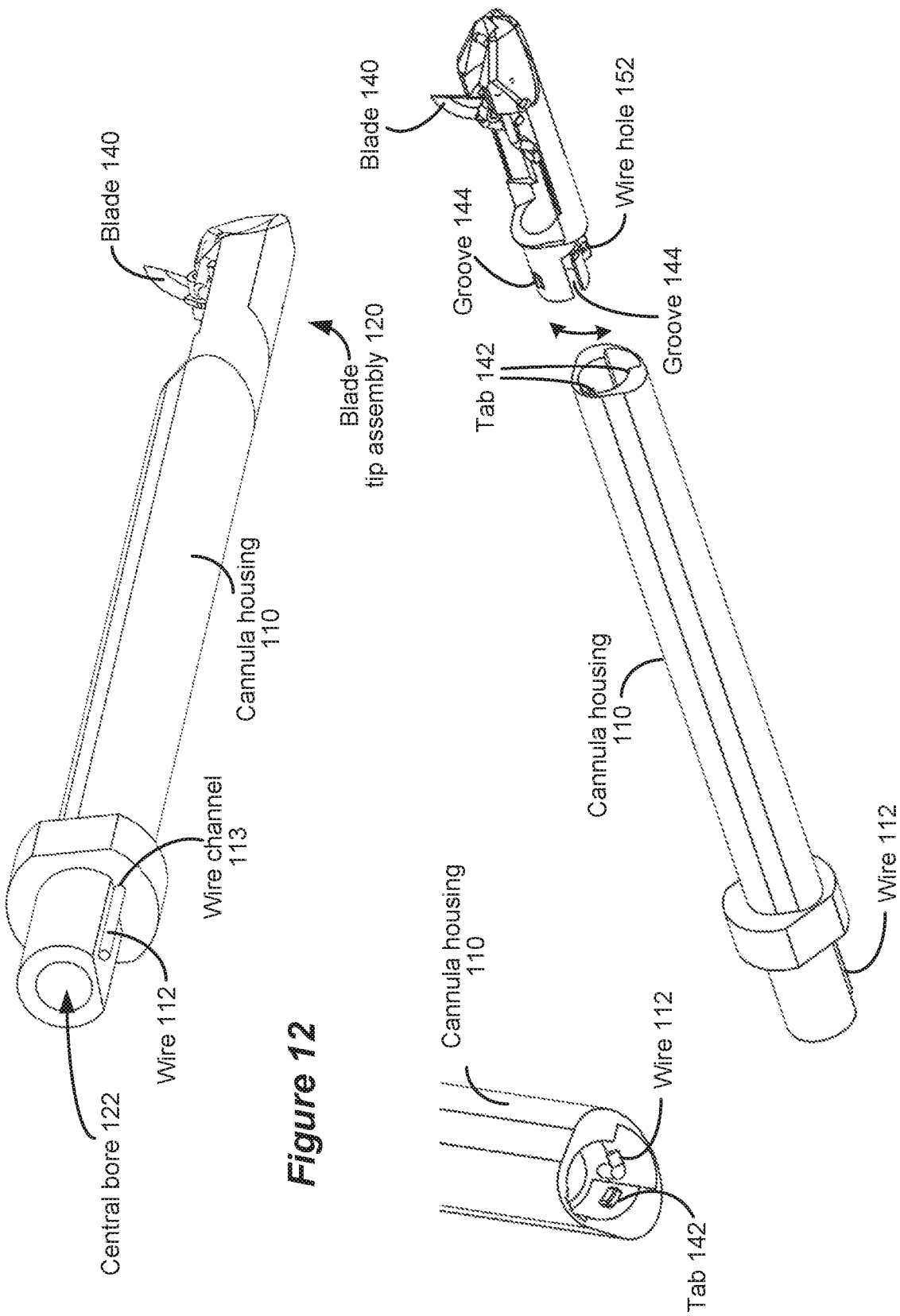
FIG. 12 shows a manner in which a blade tip assembly can be attached to the cannula.

FIG. 12 shows the blade tip assembly 120 both connected to and disconnected from the cannula housing 110, and shows the wire 112 which controls blade 140 extension and retraction. The blade tip assembly 120 is easily removable from the cannula housing 110, thus allowing the assembly to be easily replaced. It would be expected that the blade tip assembly 120 of the tool 40 would normally be replaced after each surgery, thus assuring that each new patient benefits from a blade 140 that is sharp. Fortunately, the blade tip assembly 120 is not constructed of expensive parts, and replacing the assembly 120 leaves the cannula 110 and other components intact, making component replacement more cost effective.

In one example, the blade tip assembly 120 can be connected to the cannula housing 110 by using a tab and groove arrangement. Specifically, two tabs 142 on the inside of the housing 110 can be made to meet with two right-angled grooves 144 on the blade tip assembly 120. The assembly 120 can then be turned to lock the tabs 142 in the grooves. Removal of the assembly 120 is the reverse process. It should be noted that this is only an example way in which the blade tip assembly 120 can be connected to or disconnected from the cannula housing 110, and other means could be used as well (clamps or clips, press fit arrangements not requiring rotation, etc.) When attaching or removing the blade tip assembly 120, the wire 112 is attached or removed from a wire hole 152 in a component of the assembly 120, as explained shortly with respect to FIGS. 13 and 14. In this regard, the wire 112 terminates at a right angle at an end of the cannula housing 110, as shown in FIG. 12, which allows for connection to and disconnection from the wire hole 152.

Figure 13:
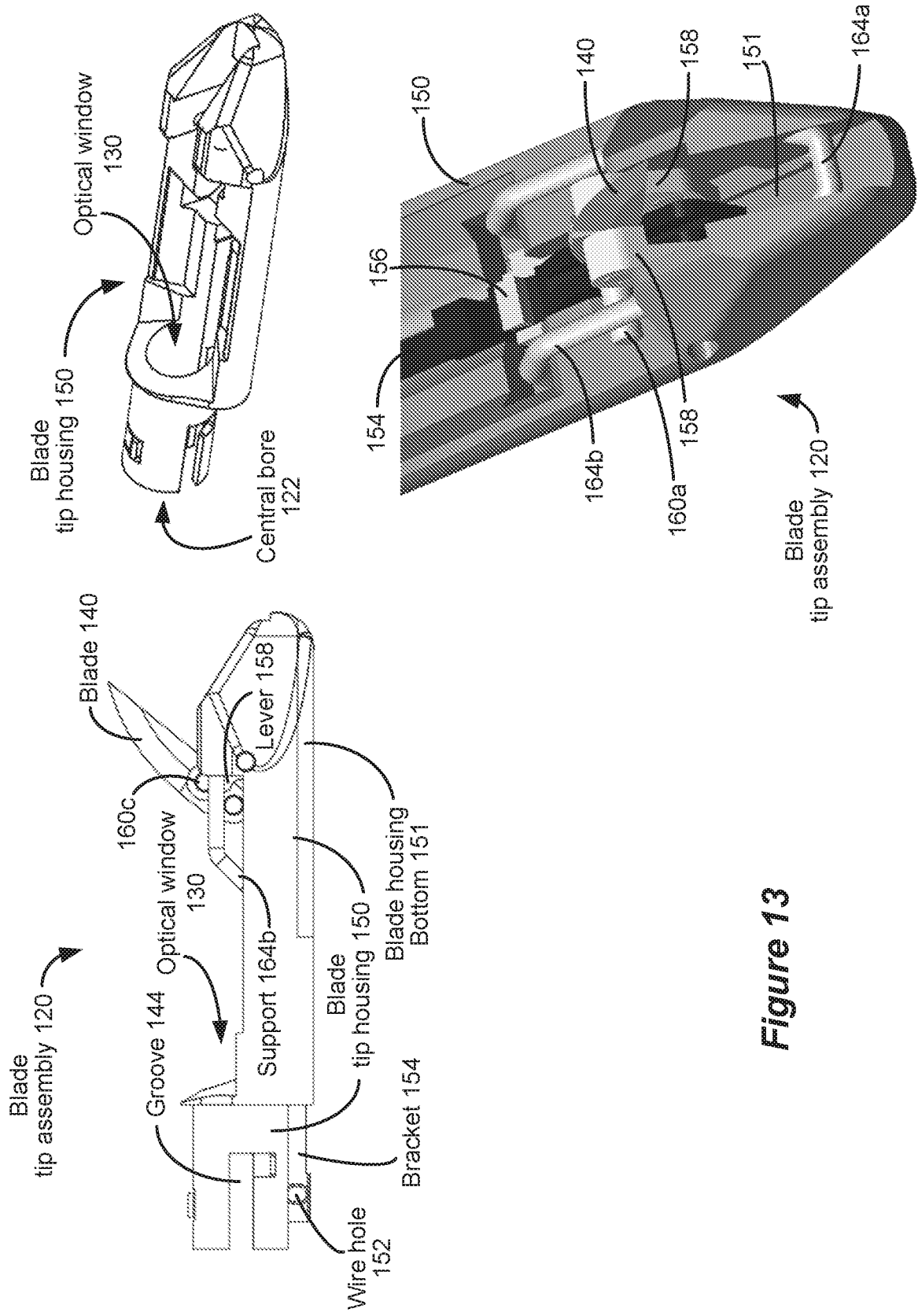
FIGS. 13 through 15 show various components in the blade tip assembly, and explains blade tip assembly operation to extend and retract a blade.

FIG. 13 shows the blade tip assembly 120 in further detail. The assembly 120 includes a blade tip housing 150, which is also shown in isolation in FIG. 13, which housing may include a blade housing bottom 151 to ease the assembly's construction. The housing 150 includes the grooves 144 discussed earlier to attach or remove the assembly 120 from the end of the cannula housing 110. Also present in the blade tip housing 150 is an optical window 130. As will be discussed later with reference to FIG. 17A, the optical window 130 provides an opening to accommodate an end of an optical assembly 170, which allows the surgeon to illuminate the patient's tissue and receive images of the tissue that can be wirelessly broadcast to a display screen.

Figure 14:
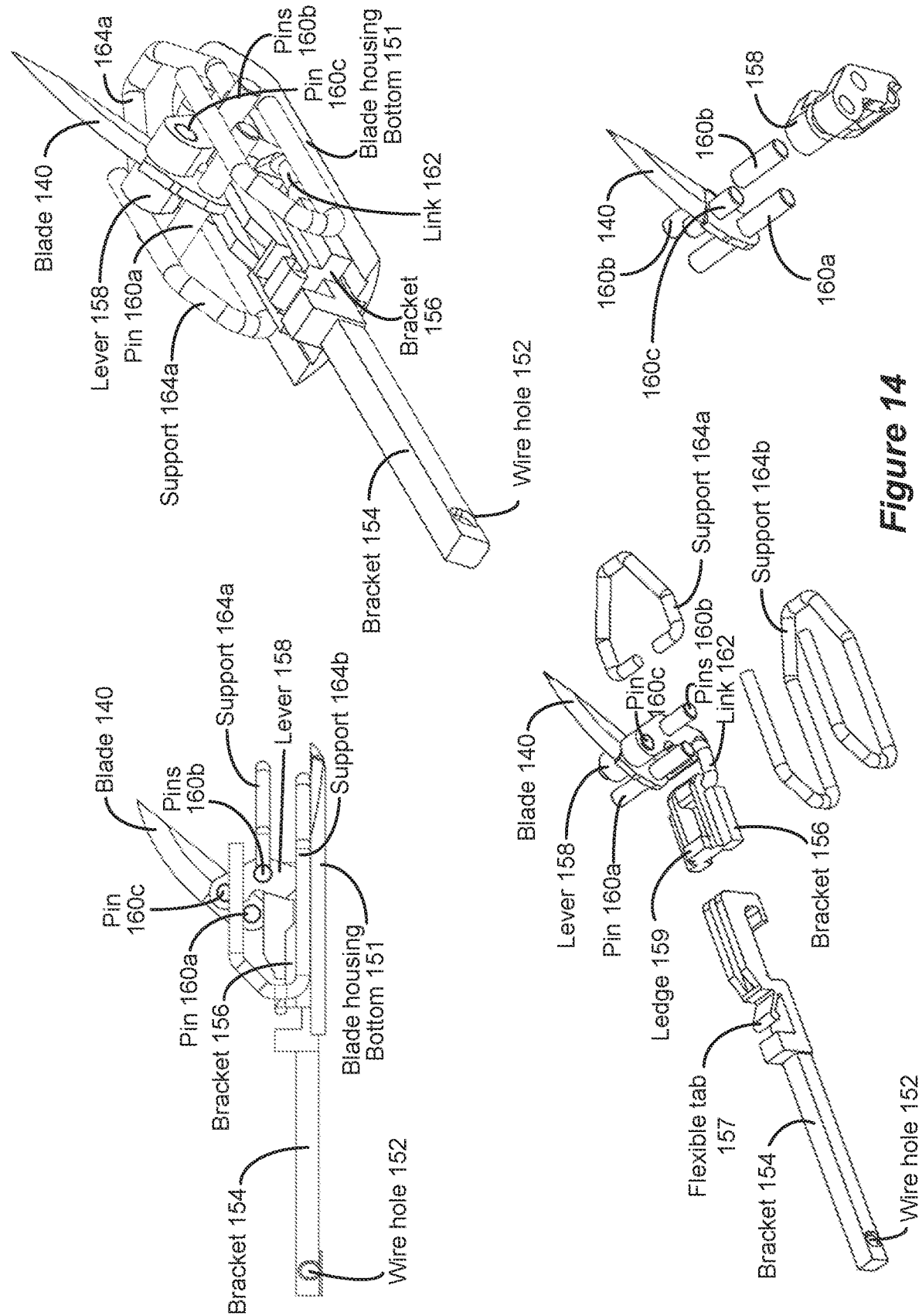

FIG. 14 shows components within the blade tip assembly 120 with the blade tip housing 150 removed for easier viewing. The blade tip assembly 120 includes supports 164a and 164b which may comprise thicker grade wire. The supports 164a and 164b are preferably bent into shape and molded into the plastic material used to form the blade tip housing 150. Support 164a provided a hard back stop for the blade 140 when it is in the fully retracted position, as perhaps best shown in FIG. 13. When in this position, the blade 140 is recessed within the blade tip housing 150, thus allowing the surgeon to introduce the cannula 46 into the patient, and to extend or retract the cannula, without risk of inadvertently cutting the patient. Support 164b restrains a pin 160a that passes through the bottom of the blade 140 to assist in extending and retracting the blade, again as explained in detail with respect to FIG. 15.

Figure 15:
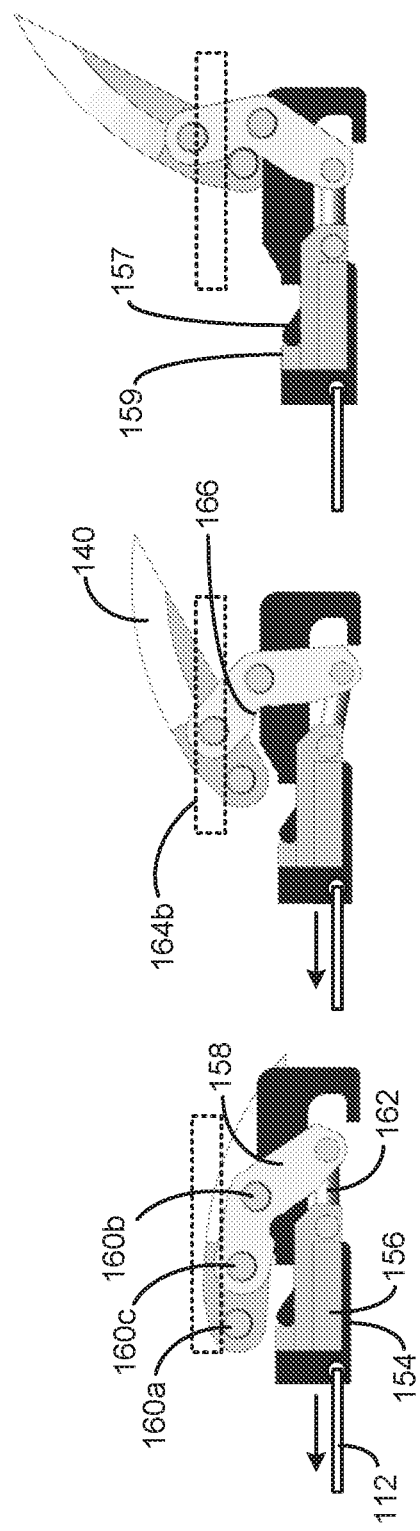

As shown in FIGS. 13 and 14, the blade 140 is bounded by a lever 158. A pin 160c passes through a rotational point in the blade 140 to fasten the blade 140 to an upper portion of a lever 158 while still allowing the blade to rotate. A center of the lever 158 is itself rotatably fastened to the sides of the blade tip housing 150 (and possibly to support 164a) by pins 160b. A lower portion of the lever 158 is attached to a link 162, which is in turn attached to a bracket 156, perhaps as best seen in FIG. 15. Bracket 156 is in turn connected to another bracket 154, which protrudes proximally from the blade tip housing 150 and includes the wire hole 152 to which the wire 112 is attached. Brackets 154 and 156 may be press fit together. It is preferable to use two different brackets for safety reasons explained later, but a single integrated bracket piece (154/156) could also be used, and is assumed for purposes of discussion.

Now that the components of the blade tip assembly 120 have been introduced, FIG. 15 shows how these components work to extend the blade 140. Again, the blade tip housing 150 and other structures have been removed for easier viewing. As noted earlier, wire 112 is connected to bracket 154/156, and so pulling wire the left 112 (by pulling trigger 48) will pull the bracket 154/156 to the left within the blade tip housing 150. This motion is transferred by link 162 to the lower portion of the lever 158. Because the lever 158 is rotatably fastened to the blade tip housing 150 by pins 160b, the lever 158 will begin to rotate clock-wise as shown. Because pin 160a through the lower end of the blade 140 is restrained by support 164b, this rotational motion will pull pin 160a to the right. Because pin 160c through the center of the blade 140 continues upwards as the lever 158 rotates, blade 140 begins to rotate counter-clockwise and thus extends away from the assembly 120, and thus can now be used to cut the patient's tissue. When the wire 112 is pulled to the right (i.e., when the trigger 48 is released), wire 112 will push the bracket 154/156 to the right to reverse the motions just described, thus retracting the blade 140 safely back into the blade tip housing 150.

As noted above, it is preferable to use separate brackets 154 and 156 to provide a useful safety feature—namely the ability to automatically retract the knife 140 to keep it from cutting if it is experiencing too much force. This could occur for example if the blade 140 is inadvertently in contact with harder tissue, such as bone, that would indicate a problem. In this regard, and as shown in FIGS. 14 and 15, bracket 154 is formed with a flexible tab 157 which meets with a ledge 159 on the bracket 156 when the two brackets are fastened together. When trigger 48 is pressed and wire 112 is pulled to the left, force is transferred from bracket 154 and bracket 156 at the flexible tab 157. Normally, the moves bracket 156 to the left, and extends the blade 140 as just described, and if the trigger 48 is pulled further, the blade can begin to cut the patient tissue, as described in detail later with respect to FIGS. 16A-16E. However, if the blade 140 encounters hard tissue, such resistance will be transferred back to bracket 156, which will now place an excessive force between its ledge 159 and the flexible tab 157 on bracket 154. If this force exceeds a threshold, the flexible tab 157 will pass over the top of the ledge 159 to relieve the pressure. When this occurs, force from the wire 112 will no longer place sufficient force on the bracket 156 to allow for blade 140 extension, and the blade 140 will fall safely back into the blade tip housing 150. Note that if this occurs, the blade tip assembly 120 will need to be replaced, but as explained earlier, this is easily and inexpensively accomplished.

Now that attachment, construction, and operation of the blade tip assembly 120 has been discussed, operation of the tool 40 is further explained with reference to FIGS. 16A-16E, which show structures within the tool 40 that are important to understand its movement (other structures have been omitted for clarity).

FIG. 16A shows the tool at rest, i.e., before pressure has been placed on the trigger 48. At this point, the spring 74 (FIG. 7) pulls the movable member 72 and the trigger 48 to which it is coupled to its right most point. The movable member 72 contacts a left edge of the ring slider 98, and so pushes the ring slider 98 to the right as well (as it slides though barrel 66; FIG. 5). The ring slider 98, as described earlier, is connected to contact beam 105 which is in turn connected to a groove on the fixed coupling 118, which is connected to the end of the cannula housing 110. Therefore, the cannula housing 110 and the blade tip assembly 120 are also pushed to their right most extent. Because the central cylinder 102 is connected (hole 91; FIG. 8) to the movable member 72, it also is biased to the right by the spring 74, and slides within the ring slider 98 and the insulator 100 (not shown). The other end of the central cylinder 102, again as described earlier, is connected to a couple 106, which has a protrusion that meets with a groove on the sliding coupling 114. Therefore, this sliding coupling 114 is also drawn to its right-most point, i.e., to the point where it hits the shoulder 111 on the cannula housing 110. As noted earlier, the sliding coupling 114 is affixed to wire 112, which is likewise forced to the right. As explained earlier with reference to FIGS. 13-15, moving the wire to the right retracts the blade 140 within the blade tip assembly 120, as shown in FIG. 16A. To summarize, in the rest position of FIG. 16A, the blade 140 is retracted and the cannula 46 is extended from the tool.

Note at rest that the sliding coupling 114 is spaced at a distance X from the fixed coupling 118 at the end of the cannula housing 110. Note also that an edge 109 of the central cylinder 102 is likewise spaced at a distance X from a right edge of the ring slider 98. Finally, note also that the optical electronics module 63 is also coupled to the movable member 72, as noted earlier and described further later with reference to FIGS. 19-20. Thus, and as shown in subsequent FIGS. 16B-16E, the optical electronics move 63 will also move with the tool as the trigger 48 is moved. Specifically, the optical electronics 63 will slide within the barrel 66 (FIG. 5).

FIG. 16B shows the position of the components after the trigger 48 has been pulled to the left by distance X. As the trigger 48 is pulled through this distance, the movable member 72 moves as does the central cylinder 102. Note that the central cylinder 102 slips though the ring slider 98, which remains in a constant position within the tool. Therefore, by virtue of contact beam 105 and fixed coupling 118, the cannula housing 110's position doesn't change, and it is still in a fully extended state. (The dotted line in FIGS. 16A-16E show a fixed reference point in the tool so that the relative movement of the components can be better appreciated). Movement of the central cylinder 102 and its couple 106 transfer to the sliding coupling 114, which similarly slides distance X until it hits the fixed coupling 118. At this point, edge 109 of the central cylinder 102 may also make contact with the right edge of the ring slider 98. As the sliding coupling 114 is pulled left, it pulls the wire 112 to the left, which as explained earlier extends the blade 140 from the blade tip assembly 120, as shown in FIG. 16B. Preferably, the blade tip assembly 120 has at this point been placed by the surgeon in a position relative to tissue to be cut, such as the transverse carpal ligament 10. Such proper placement can be assisted by use of the optical capabilities of the tool 40, which are described in detail later. To summarize, in FIG. 16B, the blade 140 is extended and the cannula 46 remains extended from the tool as it has not moved. Notice in this position that the left edge of the ring slider 98 is now spaced a distance X from the movable member 72.

At this point, and with the blade 140 fully extended, the trigger 48 can be pulled further through an additional distance Y, as shown in FIG. 16C1. Distance Y can comprise a maximum distance at which the trigger 48 can be pulled, which as noted earlier, may be determined by how far trigger rod 80 can pass within the recess 81 of the trigger (FIG. 6) before it bottoms out. At the start of distance Y, the couplings 118 and 114 are in contact, as is the edge 109 of the central cylinder 102 and the right edge of the ring slider 98. Thus, the ring slider 98 at this point also starts to move to the left as it slides within the barrel 66. This causes the cannula housing 110 (via 105, 118) to move left as well. This also pulls the blade tip assembly 120 to the left, thus allowing the already extended blade 140 to cut through the patient's tissue 10a. To summarize, in FIG. 16C1, the blade 140 is extended and the cannula 46 is retracted within the tool 40. Notice in this position that the left edge of the ring slider 98 is still spaced a distance X from the movable member 72. Notice further that because the cannula housing 110 is retracted into the housing of the tool grasped by the surgeon (i.e., upper and lower housing portions 42a and 42b), the housing does not need to move, and hence the surgeon does not need to pull the tool away from the patient in order to make the cut.

Release of the trigger 48, and the corresponding movement of the components within the tool, is shown in FIG. 16C2-16E. FIG. 16C2 is the same drawing as FIG. 16C1, showing the condition of the components when the trigger 48 is fully pressed, and is provided for reference and easy comparison to FIGS. 16D and 16E.

In FIG. 16D, the trigger 48 is released distance X to the right. The bias of the spring 74 will pull the movable member 72 to the right, which in turn moves the central cylinder 102, couple 106, and sliding coupling 114 to the right, until the sliding coupling 114 again contacts the shoulder 111 of the cannula housing 110. Because the wire 112 is connected to the sliding coupling 114, the wire is biased to the right, which as explained earlier retracts the blade 140 within the blade tip assembly 102. Because the central cylinder 102 slides through the ring slider 98, the ring slider 98 stays in its previous position, and hence so does the contact beam 105, the fixed coupling 118, the cannula housing 110, and blade tip assembly 120. To summarize, in FIG. 16D, the blade 140 is retracted and the cannula 46 remains retracted within the tool 40. Notice in this position that there is no longer a space between the left edge of the ring slider 98 and the movable member 72.

Further release of the trigger 48 through distance Y to its rest position is shown in FIG. 16E. At this point, the movable member 72 is in contact with the ring slider 98, and therefore the spring 74 will bias both the movable member 72 and the ring slider 98 to the right. Movement of the ring slider 98 also moves the cannula housing 110 and the blade tip assembly 120 through distance Y to the right. Because the position of the sliding coupling 114 on the cannula housing 110 hasn't changed, the blade remains retracted. To summarize, in the rest position of FIG. 16E, the blade 140 is retracted and the cannula 46 is extended from the tool 40. Notice further that because the cannula housing 110 is extended from the housing of the tool grasped by the surgeon (i.e., upper and lower housing portions 42a and 42b), the housing does not need to move, and hence the surgeon does not need to push the tool towards the patient to arrive at the rest position.

Optical details of the tool 40 are discussed next, starting with FIG. 17A. As shown in FIGS. 9-13, the central cylinder 102, the fixed coupling 118, the cannula housing 110, and the blade tip housing 150 are formed with a central bore 122. As shown in FIG. 17A, an optical assembly 170 can be slid into this bore 122. Preferably, the optical assembly 170 will be slidably held within the central bore 122 in the cannula housing 110. This allows the optical assembly 170 to be axially rotated around the long axis of the cannula housing 110 as described previously (using rotatable housing 104).

Holding the optical assembly 170 slidably with the central bore 122 also permits the optical assembly 170 to slide horizontally along the long axis in accordance with the various positions just described with respect to FIG. 16A-16E. Such movement of the optical assembly 170 occurs because the proximal face 170b of the optical assembly 170 is affixed to the moveable member 72 and the optical electronics module 63, as explained in detail later.

When the trigger 48 is at rest (FIG. 16A), a distal angled face 170a of the optical assembly 170 will extend slightly relative to an angled optical window 130 formed in the blade tip housing 150, as shown in FIG. 17A.

When the trigger 48 is first pulled and moves through distance X (from FIGS. 16A to 16B), the moveable member 72, the optical electronic module 63 and the optical assembly 170 (which again are all affixed) are pulled to the left relative to the extended cannula housing 110. This pulls optical assembly 170 to the left by this same distance X through the housing 110. This preferably brings the distal angled face 170a of the optical assembly 170 flush with the angled optical window 130, as shown in FIG. 17B.

When the trigger 48 is pulled further through distance Y (from FIGS. 16B to 16C1), the moveable member 72, the optical electronic module 63 and the optical assembly 170 are pulled to the left in unison with the cannula housing 110 (which now retracts). Therefore, the position of the distal angled face 170a of the optical assembly 170 remains flush with the angled optical window 130, as shown in FIG. 17B.

When the trigger 48 is partially release through distance X (from FIGS. 16C2 to 16D), the moveable member 72, the optical electronic module 63 and the optical assembly 170 are pushed to the left relative to the retracted cannula housing 110. This pushes optical assembly 170 to the right by this same distance X through the housing 110, which again extends the distal angled face 170a of the optical assembly 170 from the angled optical window 130, as shown in FIG. 17A.

When the trigger 48 is further fully release through distance Y (from FIGS. 16D to FIG. 16E), the moveable member 72, the optical electronic module 63 and the optical assembly 170 are pushed to the right in unison with the cannula housing 110 (which now extends). Therefore, the position of the distal angled face 170a of the optical assembly 170 remains extended with respect to the angled optical window 130, as shown in FIG. 17B.

It should be noted that horizontal movement of the optical assembly 170 within the cannula housing 110 (between the states shown in FIGS. 17A and 17B) do not significantly affect operation of the tool 40. The angled distal face 170a will move slightly which will slightly move the field of view 172. This is however not problematic, and if necessary, the surgeon can compensate by pushing or pulling the cannula housing 110 through the patient's tissue to adjust the horizontal view of the tissue as necessary.

FIG. 18 shows the optical assembly 170 in cross section. In one example, the optical assembly 170 includes at its center an image-receiving pathway, and includes along its perimeter a light-transmitting pathway. The light-transmitting pathway preferably comprises a plurality of fiber optical cables 180. As will be explained in detail with reference to FIGS. 19 and 20, the cables 180 receive light from the light emitters (e.g., Light Emitting Diodes, or LEDs) in the optical electronics module 63 at a terminated ends 180b of the cables 180 at the proximal end of the assembly 170, and transmit this light to terminated ends 180a at the distal end of the assembly 170. The distal end of the optical assembly 170 passes through the optical window 130 of the blade tip housing 150, where the terminated ends 180b can illuminate the patient's tissue.

The image-receiving pathway preferably comprises a sequence of silica rods 178, which form a light pipe that transmit images of the illuminated tissue from a prism 178a at the distal end of the assembly 170 to a terminal silica rod 178b at the proximal end of the assembly 170, where such images can be captured by a camera in the optical electronics modules 63. A sequence of a plurality of silica rods 178 is preferred because a single rod may be too fragile and easily broken, and further may be subject to cracking under thermal expansion, particularly when the tool is autoclaved. The prism 178a at the distal end is angled as shown, which operates to capture images generally along an axis 171 that is not parallel to axis 250 of the cannula, but instead point above the blade tip assembly 150. More generally, the angle end 170a of the optical assembly 170 forms a field of view 172 that is above the blade tip housing 150 and proximate to where the extended blade 140 and tissue to be cut can be seen. As noted earlier, the cannula housing 110 can be rotated to adjust the rotation angle of the field of view, thus allowing the surgeon more flexibility to see structures of interest.

The optical assembly 170 is preferably formed as a solid piece without air gaps, and may comprise an inner jacket 176 surrounding the silica rods 178, and an outer jacket 174 which surrounds the fiber optic cables 180 such that they are between the outer and inner jackets. The inner and outer jackets may be formed of a single layer or a combination of engineering thermoplastics, such as polysulfone (PSU), polyether ether ketone (PEEK), polyetherimide (PEI), etc. Otherwise empty spaces 173 in the assembly 170 (around the cables 180 between the jackets 174 and 176, and around the rods 178 within the jacket 176) may be filled with polymethyl methacrylate (PMMA). Note that given its optical clarity, the PMMA may be used to couple images from one silica rod 178 to the next without significant loss. After the optical assembly is formed, its proximal and distal faces, shown in FIG. 18, are preferably polished to allow for good optical transfer.

Figure 20:
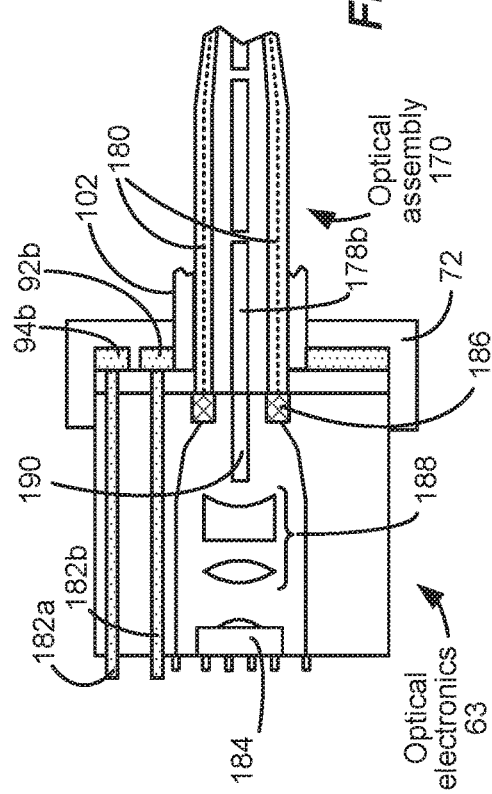

FIGS. 19 and 20 show details concerning the formation of the optical electronics module 63, and how the optical electronics module 63 can be coupled to the optical assembly 170 and to other electronics in the upper electronics cavity 41a (FIG. 2). As mentioned earlier, the optical electronics module 63 includes one or more light emitters such as LEDs 186 used to provide light to the fiber optic cables 180, and a camera 184 to receive images from the silica rods 178. The optical electronics module 63 can also include an image-receiving path, which like the optical assembly 170 can include one or more silica rods 190. Additionally, one or more corrective lenses 188 may intervene between the silica rod(s) 190 and the camera 184. Note that the camera 184 can comprise any number of small camera devices, such as those commonly used in cellular telephones to capture images. While the optical electronic module 86 is shown as integrating both illumination and image capture functionality, reality that these functions can be separated into different modules. For example, a first module can include the LEDs 186, and a second module can include the camera 184.

As shown in the picture of the face of the optical electronics module 63 in FIG. 19, components can be arranged such that the LEDs 186 match up with the terminated ends 180b of the fiber optical cables 180 at the proximal end of the optical assembly 170, and such that a terminated end of the silica rod 190 matches up with the terminal silica rod 178b at the proximal end of the optical assembly 170. Although not shown, the optical electronics module 63 may include light-blocking structures to prevent light from the LEDs 186 from reaching the image-receiving path formed by the silica rod 190, lenses 188 and camera 184.

The optical electronic module 63 further includes conductive pins 182a and 182b. Conductive pins 182a and 182b are preferably pogo pins which include spring tips at their terminations to allow the pins to be pressed in when in contact with another conductive surface. As will be explained shortly, pins 182a and 182b can be used to route power (i.e., power and ground voltages) to electronics in the upper electronics cavity 41a, and to the camera 184 and LEDs 186. In this regard, electrical terminations, such as the pins of the camera 184, the terminals of the LEDs 186, and the pins 182a and 182b, can meet with an electrical connector 192a at the end of a cable 192. Cable 192 (e.g., a ribbon cable) can pass necessary signals from these electrical components to another connector 192b at its other end, which can in turn be connected to a printed circuit board (PCB) 194 in the upper electronics cavity 41a. In this way, the PCB 194 in the upper electronics cavity 41a can receive power from pins 182a and 182b via cable 192 and its connectors. Further, such power can be routed back from the PCB 194 to components in the optical electronics module 63, such as the camera 184 and the LEDs 186. Preferably, the LEDs 186 are electrically connected in series within the body of the optical electronics module 63 (not shown), and thus only terminate at two ends at the connector 192a.

The optical electronics module 63 may generally resemble a cylinder, with its various components integrated and held together by mold injecting a material 189 around them. In one example, this material 189 may comprise PMMA or another transparent material, which as noted earlier is good to promote optical coupling in the module 63's image-receiving path.

As noted above, the optical electronics module 63 is coupled to the movable member 72, and so moves in the barrel 66 as the movable member 72 moves. The manner of this coupling is shown in FIGS. 19 and 20. As shown, the movable member can include a recess 193 to receive the module 63, which recess 193 can be formed in the movable housing member 83c (FIG. 8). Also inside this recess 193 are the inner and outer conductive rings 92b and 94b described earlier, i.e., the positive and negative power supplies (FIG. 8). When the module 63 is seated in the recess 193, and as shown in FIG. 20, pin 182a makes electrical contact with outer conductive ring 94b, which as noted earlier can carry the negative power supply voltage (e.g., ground). Pin 182b similarly makes electrical contact with inner conductive ring 92b, which as noted earlier can carry the positive power supply voltage. Note that because the module 63 moves as the trigger 48 is pulled, care should be taken to ensure that cable 192 has sufficient slack to allow for such movement. Notice that the conductive rings 92b and 94b make electrical contact to pins 182a and 182b of the optical electronic module 63 even if that module 63 rotates around the long axis through the cannula.

Further, when the optical electronics module 63 is seated, the proximal face 170b of the optical assembly 170 is brought into contact with the opposing face of the module 63. Because these opposing faces are smooth, light from the LEDs 86 transfers to the fiber optic cables 180, and images from the silica rods 178 transfer to the silica rod 190, lenses 188, and ultimately to the camera 188.

FIG. 19 shows electronic components that can be housed in the upper electronics cavity 41a on PCB 194. Significantly included is a wireless chip set 200 and an antenna 202. As image data comes into the PCB 194 from the camera 184, it may be stored (buffered) in memory if necessary (not shown), and if necessary encoded 208 with a suitable video encoding format, such as H.264. Ultimately the image data is provided to the chip set 200, which includes a transmitter, and wirelessly broadcast in accordance with a short-range RF communications protocol, such as Bluetooth, WiFi, Zigbee, Medical Device Radiocommunications Service (MedRadio), Medical Implant Communication Service (MICS), and the like, or other proprietary protocols. The antenna 202 can be formed in different manners within the housing, and may comprise a wire, slot, patch, or coil antenna, and which may operate as a dipole or monopole antenna. Chip set 200 may also include a receiver to wirelessly receive data at the tool, which may be beneficial to update its programming for instance.

As mentioned earlier, it is not necessary that such electrical components be located in the upper electronic cavity 41a in the upper housing portion 42a. Instead, necessary electronics could be included in the lower electronics cavity 41b of the lower housing portion 42b as well (FIG. 2). In this case, image data from the camera 184 can be routed by cabling through feedthrough 49 (FIG. 2) to the lower electronics cavity 41a, with PCB 45 including necessary memory, video encoders 208 and the antenna 202. Similarly, lower electronics cavity 41a may be unnecessary, and instead the battery 47 could be included in the upper electronics cavity 41b. This would simplify tool design, and may make the inclusion of positive and negative conductors 92 and 94 (FIG. 8) in the movable member 72 unnecessary.

Because the CTR tool 40 is designed to be cleaned and sterilized using autoclave technology, the electronics may be treated in a manner to withstand the high temperatures and pressure provided by the autoclave. For example, the PCBs and their various circuitry could be overcoated with a high-temperature plastic. Note that the battery 47 is preferably removed before autoclaving the tool 40, because batteries will typically be unable to withstand the high heat autoclaving provides.

FIG. 21 shows components of the CTR tool 40 system, and shows the wireless transfer of real-time video image data 205 from the tool 40. In this example, a receiver/decoder device 215 is coupled to a display 210, such as to one of its ports. The receiver/decoder device 215 includes an antenna 209 for wirelessly receiving the wireless data 209, a chip set 207 compliant with the communications standard used (e.g., Bluetooth), and a video decoder 208 to remove the video encoding (208) used to format the data 205. Raw video images 211 may then be provided to the display 210 to allow the surgeon to visualize the tissue being cut by the blade 140 in real time. (In reality, the "real time" images may be provided to the display with some small amount of latency, but this would not significantly hamper the surgeon and may not even be noticeable). Note that modern-day displays 210 may include all or parts of the receiver/decoder 215. In this case, a separate receiver/decoder 215 may not be necessary.

Also shown in FIG. 21 as part of the system is an autoclave 220 used to sterilize the tool 40. In this regard, after use of the tool with a particular patient, the battery 47 can be removed by removing the cover 51 (FIG. 2) from the lower housing portion 42a. In this regard, the battery 47 may fit into the lower electronics cavity 41a like a cartridge, similar to what occurs in pocket cameras for example, which allows the battery 47 can easily slide out of the cavity. Further, the used blade tip assembly 120 can be discarded prior to autoclaving. (Alternatively, the blade tip assembly 120 could be subject to autoclaving sterilization as well, but this might distort its plastic and metal components due to unexpected thermal expansion).

Thereafter, the tool 40 (including the housing, the cannula, the at least one optical electronic module, the optical assembly, and the wireless transmitter and antenna still in an assembled state) may be cleaned of remnants (e.g., blood) and rinsed with water. Because the tool 40 at this stage (minus the battery and the blade tip assembly) is made of high temperature materials, the tool can then be placed in the autoclave 220 without further disassembly, where it can be heated to 120 degrees Celsius in the presence of pressurized steam for 30 minutes. Afterwards, the tool 40 may be placed in a sterilized bag until its ready for its next use, at which time the battery 47 can be reinserted and a new blade tip assembly 120 coupled to the end of the cannula 46. Care should be taken when introducing these components to the tool 40 after autoclaving to ensure proper sterility. For example, the possibly unsterile battery should not contact the outer shell of the tool, and a new blade tip assembly 120 (presumably already in a sterilized bag) should be affixed with gloves to avoid contamination.

While disclosed to this point as useful in Carpal Tunnel Release (CTR) surgery, it should be understood the use of the tool is not so limited. The tool could be used in other contexts in which it is necessary to cut tissue within a patient, for example in cubital tunnel release surgery, other types of nerve decompression surgeries, or in endoscopic surgery more generally.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A surgical tool, comprising:
   a housing comprising one or more housing portions, wherein the housing comprises a handle graspable by a surgeon, wherein the handle includes a trigger;
   a cannula emanating from the housing and defining a first long axis, wherein the cannula is configured for insertion within a patient, wherein a distal end of the cannula comprises a blade tip assembly with a blade, wherein the blade tip assembly includes an optical window;
   an actuator within the housing, wherein the actuator moves in a first direction responsive to depressing the trigger in the first direction and moves in a second opposite direction responsive to releasing the trigger in the second direction, wherein the first and second directions are parallel to the first axis;
   at least one optical electronics module within the housing, where the at least one optical electronics module comprises one or more light emitters configured to provide illumination, and a camera;
   an optical assembly within the housing having a proximal end coupled to the at least one optical electronics module and a distal end proximate to the optical window, wherein the optical assembly includes at least one first optical path configured to provide the illumination to the patient's tissue proximate to the optical window, and at least one second optical path configured to transmit images of the patient's tissue proximate to the optical window to the camera, wherein the at least one optical electronics module and the optical assembly are configured to move within the housing in the first direction when the trigger is depressed and in the second direction when the trigger is released;
   a wireless transmitter and antenna within the housing, wherein the wireless transmitter is configured to wirelessly transmit via the antenna the images received at the camera to a display; and
   a battery within the housing configured to provide power to the light emitters, the camera, and the wireless transmitter.

2. The surgical tool of claim 1, wherein the housing comprises an upper housing portion and a lower housing portion that are connectable to and disconnectable from one another.

3. The surgical tool of claim 2, wherein the upper housing portion has a second long axis parallel to the first long axis, and wherein the lower housing portion has a third long axis that is not parallel to the second long axis.

4. The surgical tool of claim 3, wherein the third long axis is substantially perpendicular to the second long-axis.

5. The surgical tool of claim 1, wherein the trigger is depressible along a fourth axis parallel to the first long axis.

6. The surgical tool of claim 1, wherein the actuator includes at least one spring configured to bias the trigger to a rest position when the trigger is not depressed.

7. The surgical tool of claim 6, wherein when the trigger is in the rest position, the cannula is extended from the housing and the blade is retracted into the blade tip assembly.

8. The surgical tool of claim 7, wherein the trigger is configured to be depressed from the rest position then to a first intermediate position and then to a fully depressed position, wherein when the trigger is depressed from the rest position to the first intermediate position, the blade is extended from the blade tip assembly and the cannula remains extended from the housing.

9. The surgical tool of claim 8, wherein when the trigger is depressed from the first intermediate position to the fully depressed position, the blade remains extended from the blade tip assembly and the cannula is retracted into the housing.

10. The surgical tool of claim 9, wherein when the trigger is configured to be released from the fully depressed position then to a second intermediate position and then to the rest position, wherein when the trigger is released from the fully depressed position to the second intermediate position, the blade is retracted into the blade tip assembly and the cannula remains retracted into the housing.

11. The surgical tool of claim 10, wherein when the trigger is released from the second intermediate position to the rest position, the blade remains retracted into the blade tip assembly and the cannula is extended from housing.

12. The surgical tool of claim 1, wherein the blade tip assembly is configured to be connectable to and disconnectable from the distal end of the cannula.

13. The surgical tool of claim 1, wherein the cannula includes a wire, and wherein the actuator is configured to pull or push the wire to extract and release the blade from the blade tip assembly.

14. The surgical tool of claim 1, wherein the second optical path is located in a center of the optical assembly, and wherein the first optical path surrounds the second optical path.

15. The surgical tool of claim 1, wherein the first optical path comprises a plurality of fiber optic cables.

16. The surgical tool of claim 1, wherein the second optical path comprises a series of silica rods.

17. The surgical tool of claim 1, wherein the distal end of the optical assembly is angled to provide a field of view with a fifth axis which points above the blade tip assembly and that is not parallel to the first long axis.

18. The surgical tool of claim 1, wherein the wireless transmitter is configured to wirelessly transmit the images using a short-range communications protocol.

19. The surgical tool of claim 1, wherein the battery is configured to be removable from the tool.

20. The surgical tool of claim 19, wherein when the battery is removed from the tool, the tool is configured to be sterilized by autoclaving, with the housing, the cannula, at least one optical electronic module, the optical assembly, and the wireless transmitter and antenna in an assembled state in the tool.

21. A surgical tool, comprising:
   a housing comprising one or more housing portions, wherein the housing comprises a handle graspable by a surgeon, wherein the handle includes a trigger;

a cannula emanating from the housing and defining a first long axis, wherein the cannula is configured for insertion within a patient, wherein a distal end of the cannula comprises a blade tip assembly with a blade, wherein the blade tip assembly includes an optical window;

an actuator within the housing, wherein the actuator is responsive to depressing and releasing the trigger, wherein the actuator includes at least one spring configured to bias the trigger to a rest position when the trigger is not depressed, wherein when the trigger is in the rest position the cannula is extended from the housing and the blade is retracted into the blade tip assembly, wherein the trigger is configured to be depressed from the rest position then to a first intermediate position and then to a fully depressed position, wherein when the trigger is depressed from the rest position to the first intermediate position, the blade is extended from the blade tip assembly and the cannula remains extended from the housing, wherein when the trigger is depressed from the first intermediate position to the fully depressed position, the blade remains extended from the blade tip assembly and the cannula is retracted into the housing, at least one optical electronics module within the housing, where the at least one optical electronics module comprises one or more light emitters configured to provide illumination, and a camera;

an optical assembly within the housing having a proximal end coupled to the at least one optical electronics module and a distal end proximate to the optical window, wherein the optical assembly includes at least one first optical path configured to provide the illumination to the patient's tissue proximate to the optical window, and at least one second optical path configured to transmit images of the patient's tissue proximate to the optical window to the camera;

a wireless transmitter and antenna within the housing, wherein the wireless transmitter is configured to wirelessly transmit via the antenna the images received at the camera to a display; and a battery within the housing configured to provide power to the light emitters, the camera, and the wireless transmitter.

\* \* \* \* \*